(12) United States Patent
Zhao et al.

(10) Patent No.: US 9,523,074 B2
(45) Date of Patent: Dec. 20, 2016

(54) SUB-TOTIPOTENT STEM CELL PRODUCT AND APPARENT HEREDITARY MODIFYING LABEL THEREOF

(75) Inventors: Chunhua Zhao, Beijing (CN); Jing Li, Beijing (CN); Hongling Li, Beijing (CN); Jianhe Chen, Beijing (CN); Qin Han, Beijing (CN); Kanghua Li, Beijing (CN); Jing Wang, Beijing (CN)

(73) Assignee: NEWISH TECHNOLOGY (BEIJING) CO., LTD., Beijing (CN)

( * ) Notice: Subject to any disclaimer, the term of this patent is extended or adjusted under 35 U.S.C. 154(b) by 99 days.

(21) Appl. No.: 13/992,619

(22) PCT Filed: Dec. 2, 2011

(86) PCT No.: PCT/CN2011/083380
§ 371 (c)(1),
(2), (4) Date: Sep. 3, 2013

(87) PCT Pub. No.: WO2012/075912
PCT Pub. Date: Jun. 14, 2012

(65) Prior Publication Data
US 2014/0287930 A1    Sep. 25, 2014

(51) Int. Cl.
*C12N 5/074* (2010.01)
*C12Q 1/68* (2006.01)
*C12N 5/077* (2010.01)
*C12N 5/0775* (2010.01)
*G01N 33/68* (2006.01)
*G01N 33/569* (2006.01)

(52) U.S. Cl.
CPC ............ *C12N 5/0607* (2013.01); *C12Q 1/6881* (2013.01); *G01N 33/56966* (2013.01); *G01N 33/6875* (2013.01)

(58) Field of Classification Search
None
See application file for complete search history.

(56) References Cited

U.S. PATENT DOCUMENTS

2010/0304489 A1* 12/2010 Geijsen et al. ............... 435/455

OTHER PUBLICATIONS

Blin et al, A purified population of multipotent cardiovascular progenitors derived from primate pluripotent stem cells engrafts in postmyocardial infarcted nonhuman primates, The Journal of Clinical Investigation, p. 1-15, 2010.*
"Epigenetic Signatures Associated with Different Levels of Differentiation Potential in Human Stem Cells", by Aranda et al., PLOS One, vol. 4, Issue 11, pp. 1-14, Nov. 2009.
"Programming Differentiation Potential in Mesenchymal Stem Cells", by Collas, Epigenetics, vol. 5, Issue 6, pp. 476-482, Aug. 16, 2010.
"Promoter DNA Methylation Patterns of Differentiated Cells are Largely Programmed at the Progenitor Stage", by Sorensen et al., The American Society for Cell Biology, Molecular Biology of the Cell, vol. 21, pp. 2066-2077, Jun. 15, 2010.

\* cited by examiner

*Primary Examiner* — Maria Marvich
(74) *Attorney, Agent, or Firm* — Ice Miller LLP

(57) ABSTRACT

Provided are a sub-totipotent stem cell product and epigenetic modification label thereof, a method for inducing the generation of the sub-totipotent stem cell product and identification for the epigenetic modification label of the differentiation potential of stem cells. Also provided is a use of histone modification states of sub-totipotent genes and/or differentiation related genes to predict the epigenetic modification label of the differentiation potentials of stem cells.

7 Claims, 10 Drawing Sheets

SUB-TOTIPOTENT STEM CELL PRODUCT AND APPARENT HEREDITARY MODIFYING LABEL THEREOF

FIELD OF THE INVENTION

The present invention relates to a sub-totipotent stem cell product, a method for inducing the generation of the sub-totipotent stem cell product and the identification of the epigenetic modification labels of differentiation potential of stem cells. Also, the present invention relates to a method for predicting the differentiation potential of stem cells, and use of histone modification states of sub-totipotent genes and/or differentiation related genes as an epigenetic modification label for predicting differentiation potential of stem cells.

BACKGROUND

Stem cells are the source of tissue regeneration. Stem cells, depending on the order they appear along the process of ontogeny, can be divided into embryonic stem cells (ESCs) and adult stem cells (ASCs). Depending on the differences in differentiation potential, they can also be divided into totipotent stem cells, pluripotent stem cells, multipotent stem cells and unipotent stem cells. ASCs, depending on their histogenesis, can also be divided into hematopoietic stem cells, bone marrow mesenchymal stem cells, neural stem cells, muscle stem cells, and the like. Some transcription factors can be introduced into animal or human somatic cells with gene transfection techniques, allowing the induced somatic cells to be reconstituted into ESC-like pluripotent stem cells, which are referred as induced pluripotent stem cells (iPSCs) [1,2]. ESCs, ASCs, and iPSCs exhibit different advantages and limitations in clinical applications, such as stages of development, origins and how they were collected, and the like. ESCs possess pluripotency differentiation; however, ethical issues, immunologic rejection, and tumorigenicity severely hinder the clinical research and application thereof. iPSCs possess a similar capacity for differentiation with that of ESCs, iPSCs still have tumorigenicity, the efficiency of generating iPSCs by inducing adult cells is extremely low, and the resulting iPSCs through induction has higher canceration rate. These factors greatly decrease safety in clinical applications. The sources of ASCs are very broad and ASCs neither exhibit tumorigenicity nor present ethical issues. It is traditionally considered that ASCs belong to pluripotent stem cells or unipotent stem cells. In recent years, experimental evidence show that ASCs have "plasticity" and not only can differentiate into specific types of cells in a specific pedigree, but also have the capability of differentiating into other pedigrees, which are irrelative in development. This suggests that ASCs have more potential of differentiation than people previously imagined [3-5].

So far, ASCs do not possess unified phenotypes, culture conditions and methods for identification due to the numerous sources. ASCs derived from various tissues show different potential for differentiation. These factors make the studies of ASCs complicated and confusing. It is difficult to establish a relatively homogeneous cell line, resulting [in further difficulties in clinical applications.

Epigenetic modifications generally include DNA methylation, histone modification and RNA modification; while histone modification includes methylation, acetylation, phosphorylation and ubiquitination with the modification sites usually located at the N-terminal of histone. These modifications can change the state of chromatin and even affect the binding of transcription factors to a DNA sequence by affecting the affinity of histone with DNA. These modifications show a similar impact on the regulation of gene expression with DNA genetic codes, and thus are referred to as the "histone code". Methylation of histone refers to methylation occurring at arginine or lysine residues at the N-terminal of H3 and H4 histones, which is mediated by histone methyltransferase. Methylation of lysine of histone has become an important regulatory mechanism of transcription and plays an important role in the formation of heterochromatin, inactivation of X chromosome, genomic imprinting, repair of DNA damage, and regulation of gene transcription [6-10]. The triple-methylation of lysine of Histone H3 at position 4 (H3K4me3) is generally associated with the activation of promoter [11], while the triple-methylation of lysine of Histone H3 at position 27 (H3K27me3) is generally associated with the silencing of the expression of promoter [12, 13]. In gene promoter region, the coexistence of the two histone modification states, H3K4me3 and H3K27me3, are referred as bivalent modification. Such a bivalent modification maintains the expression of the gene at a relatively low level and maintains the gene in a state of "being ready for transcription". Such a state allows the gene to make a rapid response to appropriate stimulations (such as activation or inhibition of transcription and the like) [14-17].

Recently, growing numbers of studies pay attention to the role of methylation of lysine of histone played in embryonic development. Studies in zebrafish found that the genome becomes inactivated after fertilization and re-initiates transcription after maternal-zygotic transition [18-20]. The analytical results of triple-methylation of lysine in genomic histone H3 show that neither histone H3K27me3 inhibitory modification or H3K4me3 activating modification are detectable before transition. 80% genes show H3K4me3 modification after the transition is accomplished and the genome is activated, wherein some un-activated genes related to regulation of development also have H3K27me3 modification. These results indicate that bivalent or monovalent modification profile of chromatin histone H3 established during maternal-zygotic transition is likely to be associated with the establishment of totipotency [21]. Previous studies found that in mouse ESCs, co-localization of H3K4me3 and H3K27me3 is located within highly conserved regions consisting of about 2.5% genome, suggesting that such a bivalent modification state plays an important role in maintaining a state of "being ready for" activation in stem cells [14]. Studies on histone modifications in human ESCs found that, around the promoter, H3K4me3 modification widely spreads, while H3K27me3 is present only within 10% of gene promoter regions. In addition, the regions having H3K27me3 modification are also modified by H3K4me3 simultaneously. These genes modified by bivalent modification will be preferentially activated during ESC differentiation, suggesting that the existence of bivalent modification may be essential to maintain the development-related genes in a balanced state and to prepare for the future activation [15]; while those genes without any modifications will be in a state of suppression, and are completely silenced. A database established with ChIP-Seq detection results is used to analyze H3K4me3 and H3K27me3 modifications in multipotent neural the progenitor cells (NPCs), murine embryonic fibroblasts (MEFs) and primary human T cells. In NPCs or MEFs, there is a decline in the number of bivalently modified genes [10, 17]. This suggests that most of bivalently modified regions are specific to ESCs [14]. However, recent analysis in methylation profile of genome-wide histone shows that such bivalently modified regions are found in differentiated cells (such as T cells and MEFs). Thus, bivalent modification is not specific to ESCs [10 17, 22]. Histones of genes without any modification previously are re-modified by methylation, although there is a decline in the number of bivalently modified genes in human T cells when compared with ESCs, suggesting that such changes of the modification of histone may be associated with the specialization of T-cell and the inhibition of other pedigrees [15].

Although studies suggest that methylation of histone plays an important role in heterochromatin formation, inactivation of X-chromosome, genomic imprinting, repair of DNA damage and regulation of gene transcription, that methylation sites of histone are highly conserved among different species, and cells with different differentiation potentials have different profiles of methylation modification of histone, so far, people know little of the role and significance of methylation modification of histone in cell differentiation. Epigenetic regulation is a dynamic process, which makes epigenetic research complicated. In recent years, along with the rapid development of sequencing technology and the decrease in cost, the technology (ChIP-Seq) combining chromatin co-immunoprecipitation with sequencing has a wide range of applications [23, 24].

Stem cell transplantation can be used for the treatment of Parkinson's disease, cardiomyopathy, liver disease, for the induction of osteogenesis for the treatment of bone defects, and skin materials needed in the treatment of extensive burns, and the like. ASCs have advantages such as autologous, showing no signs of immunologic rejection during transplantation of tissue differentiated therefrom, and have a wide range of induced tissue types differentiated therefrom. Thus, ASCs show broad application prospects and are hopeful to become the main force in the stem cell transplantation treatment of various terminal stage organ diseases in the future. However, there are safety issues in stem cell transplantation. For example, it is reported that ESCs transplanted into the heart for the treatment of coronary heart disease may result in teratoma; the application of skeletal muscle stem cells may result in a rick of malignant arrhythmias; and bone marrow cells after being transplanted show severe myocardial calcification. Therefore, the successful treatment of stem cell transplantation depends on two important factors: (1) obtaining, purifying and amplifying seed stem cells in vitro; and (2) providing specific and functional differentiation of stem cells, in accordance with therapeutic purposes, in vivo. It is vital for stem cell transplantation treatment to not only control proliferation so as to avoid tumorigenesis but also initiate desired pathways to differentiate at a proper time. However, to address the series of issues, such as the acquisition of stem cells with appropriate potential of differentiation, identification according to therapeutic purposes, and transplantation into a body to provide specific differentiation at a proper time without the occurrence of teratoma, a set of indicators is needed to accurately identify and evaluate the differentiation potential, differentiation stage of stem cells and whether or not the stem cells can differentiate in a controllable and specific fashion and the like. Therefore, the prospect of pluripotent stem cells in clinical applications depend on their differentiation potential. The existing methods for examining the differentiation potential of stem cells derived from certain tissue are performed mainly by inducing differentiation and observing whether the stem cells can differentiate towards as many triploblastic pedigrees as possible. Such methods are time-consuming and require a lot of manpower and resources.

Chromatin Immunoprecipitation (ChIP) is the most important way for detecting histone modifications. ChIP is also known as binding site analysis, which is a powerful tool to study the in vivo interactions between proteins and DNA, and is usually used to study the binding site of transcription factors or specific modification sites of histone. ChIP is a method developed based on in vivo analysis. Its basic principle is to fix protein-DNA complex under living cell state and randomly cut the complex into small chromatin fragments within a range of certain lengths, and then precipitate the complex by using an immunology method, specifically enrich DNA fragments bound by target protein, and obtain information about protein-DNA interaction by the purification and detection of target fragments. Target fragments can be detected by tiling array or high-throughput sequencing, wherein the former is known as ChIP-on-chip while the latter is known as ChIP-Seq. The combination of ChIP and second-generation sequencing technology, ChIP-Seq technology, is able to highly efficiently detect the DNA segments interacting with histone or transcription factor and the like on a genome-wide scale.

The principle of ChIP-Seq is as follows: specifically enrich DNA fragments bound by target protein with ChIP; purify the fragments and establish a library; and subject the enriched DNA fragments to high-throughput sequencing. A researcher can obtain information about DNA segments interacting with histone or transcription factor and the like on a genome-wide scale by precisely locating millions of sequence tags in the genome.

ChIP-Seq data is the result of DNA sequencing, and provides researchers with resources for the further exploration of biological information. Researchers can carry out their studies in the following areas:

(1) Determine what kind of histone modification will exist at certain site of DNA strand;

(2) Detect the precise location of the binding site of RNA polymerase II and other trans-factors within the genome;

(3) Study the relationship between histone covalent modification and gene expression;

(4) Research CTCF transcription factors.

Therefore, the most basic material and indicators for broad clinical applications of stem cells can be provided if stem cells having appropriate differentiation potential can be obtained by using specific isolation, induction and screening systems. Genome-wide histone methylation profiles of stem cells at multiple grades can be studied by utilizing the role of "histone methylation code" in the prediction of cell differentiation and by using the combination of ChIP detection and bioinformatics (ChIP-Seq). The relationship between histone methylation modification and differentiation potential of stem cells can be found, the unified phenotype, culture condition and method for identification can be established for ASCs, and a set of indicators can be established in order to accurately identify and evaluate the differentiation potential, differentiation stage of stem cells, and determine whether or not stem cells can differentiate in a controllable and specific fashion. FIG. 7 is the technical schematic diagram of present invention.

BRIEF DESCRIPTION

Accordingly, the objective of the present invention is to obtain sub-totipotent cells through induction, which present epithelioid morphology, have Flk1 positive phenotype, and differentiation potential towards triploblastic multi-pedigrees, without tumorigenicity. The acquisition of such cells provide ideal seed cells for clinical regeneration and repair treatment.

Another objective of the present invention is to find out the relationship between histone methylation modification and differentiation potential of stem cells, thereby providing a powerful tool for quick and accurate determination of differentiation potential of stem cells.

Accordingly, the first aspect of the present invention is to provide a sub-totipotent stem cell product, characterized in that said sub-totipotent cell product presents epithelioid morphology, Flk1+ phenotype, an absence of tumorigenicity. The cell derived from the individual clone shows differentiation potential towards tissue cells derived from triploblastic origin upon induction. Preferably, the primary methylation modification states of the totipotent genes in the cell including: Oct4, Nanog, c-Myc, Sall4, Sox2, Klf4; ectoderm early differentiation related genes including: Hoxa1, Gbx2, Six1 and Olig3; mesendoderm early differentiation related genes T, Pgdfrα, Eomes, Tbx6 and Mix11; mesoderm early differentiation related genes Kdr, Hand1, Gata4 and Mesp2; definitive endoderm early differentiation related genes Onecut1, Prox1, Foxa1, Foxa2, Sox7, Sox17, Pdx1 and Gsc are activated modification or bivalent modification of coexistence of H3K4me3 and H3K27me3.

The second aspect of the present invention relates to a method for producing the sub-totipotent stem cell product as described above, comprising the following steps:

A) aMSC or bMSC or mesenchymal stem cells derived from other tissues are isolated with conventional methods, B) aMSC or bMSC or mesenchymal stem cells derived from other tissues are inoculated into the wells of 96-well plate at a density of 1 cell/well, individual clones are allowed to grow, followed by a further proliferation of said individual clones, C) Cells obtained after the further proliferation of said individual clones are used as seed cells and are cultivated for 4-6 h until complete adherence, and then No. 1 inducing medium is added and the induction is maintained for 1 day. The medium is replaced with No. 2 inducing medium and induction is maintained for another 4 days. Sub-totipotent stem cells (i.e. Flk1 positive MSC) are harvested, wherein said No. 1 inducing medium contains 1-100 ng/ml activin A+1-500 ng/ml Wnt3a+0.1-20% FBS+HG-DMEM, preferably 5-50 ng/ml activin A, more preferably 10-30 ng/ml activin A; preferably 50-300 Wnt3a, more preferably 100-300 ng/ml Wnt3a; preferably 2-10% FBS, more preferably 5-8% FBS, said No. 2 inducing medium contains 1-100 ng/ml activin A+1-500 μM RA+0.1-50% FBS+HG-DMEM, 5-50 ng/ml activin A, more preferably 10-30 ng/ml activin A; preferably 20-400 μM RA, more preferably 50-200 μM RA. The resulting sub-totipotent stem cells having epithelioid morphology are subjected to RT-PCR detection, immunofluorescence staining detection and Western Blot detection, wherein indicators for said immunofluorescence staining detection include Foxa2, Sox17, Kdr, Tbx6, Eomes, Gsc, T, Sox1, Pax6, indicators for said Western Blot detection include Foxa2, Sox17, T, Gsc, Epcam, Vimentin. The obtained stem cells are determined whether they possess the important gene phenotype markers indicating differentiation potential towards three germ layers and have a higher inducing efficiency, said important gene phenotype markers refer to definitive endoderm markers Foxa2, Sox17; mesendoderm markers Gsc, T, Eomes; mesoderm markers Kdr, Tbx6; ectoderm markers Sox1, Pax6, wherein the efficiency of Foxa2, Sox17 positive definitive endoderm cell is more than 90%.

The third aspect of the present invention relates to a method for determining whether or not a stem cell product is a sub-totipotent stem cell product, comprising the following steps:

1) Target stem cells are obtained and determined whether or not the cell morphology thereof is epithelioid morphology;

2) Stem cells are determined whether or not they are Flk1 positive;

3) The differentiation potential thereof is detected with RT-PCR, immunofluorescence staining and Western Blot method, wherein indicators for said immunofluorescence staining detection include Foxa2, Sox17, Kdr, Tbx6, Eomes, Gsc, T, Sox1, Pax6, indicators for said Western Blot detection include Foxa2, Sox17, T, Gsc, Epcam, Vimentin;

4) Stem cells are transplanted into SCID mice and determined whether or not they result in teratoma;

5) Induced differentiation towards triploblastic multipedigree is performed; as for induced neural differentiation: N2/B27, 20 ng/ml EGF and 50 ng/ml IGF-1 are added into DMEM/F12 (DF12) 1:1 basal medium, after 2 weeks of induction, 30 ng/ml NT3 and 10 ng/ml bFGF are added; after 2 weeks, 30 ng/ml NT3 and 10 ng/ml BDNF are added to induce for another 7 days; as for adipogenic differentiation: 10% FCS, 1 μm dexamethasone, 0.5 mM IBMX, 1 mM ascorbic acid are added into DMEM basal medium and the cells are induced for 8 days; as for osteogenic differentiation: 10% FCS, 10 mM beta-sodium glycerophosphate, 10 nM dexamethasone and 0.2 mM ascorbic acid are added into DMEM basal medium and the cells are induced for 8 days; as for induced liver epithelial differentiation: 20 ng/ml HGF, 10 ng/ml FGF-4, ng/ml EGF and 2% FBS are added into basal medium and the cells are induced for 3 weeks; as for induced hematopoietic cell differentiation: 150 ng/mL SCF and 200 ng/mL G-CSF are added into basal medium and the cells are induced for 7 days, the cells are collected and plated into serum-free methylcellulose semi-solid medium, said medium contains 1% BSA, 50 ng/mL BMP-4, 50 ng/mL IL-6, 50 ng/mL SCF, 50 ng/mL Flt-3L, 10 ng/mL G-CSF, 10 ng/mL TPO; 10 μg/mL EPO, 200 μg/mL transferrin, 2 mM L-glutamine, 0.1 mM beta-mercaptoethanol, 1% non-essential amino acids, cells are induced for 9 days, and then the cells are collected and methylcellulose is removed by washing, 5000 cells are counted and re-plated into serum-containing methylcellulose semi-solid medium allowing induction for another 14 days.

6) The sub-totipotent and tissue differentiation related genes in said stem cells are detected for their histone methylation state so as to predict the differentiation potential of said stem cells, the method is shown as following:

1) All DNA samples which bind to specific antibodies against the triple-methylated lysine of Histone H3 at position 4 and against the triple-methylated lysine of Histone H3 at position 27 are obtained from said stem cells with ChIP technique using said antibodies;

2) The DNA samples obtained with ChIP are subjected to high-throughput sequencing so as to obtain genome-wide histone methylation modification profile of target stem cells and/or to design primers specific to target genes, the DNA samples described above is used as substrates, and PCR reactions are performed to obtain histone methylation modification states of target genes; and wherein, the presence of triple-methylation of lysine of Histone H3 at position 4, or coexistence of triple-methylation of lysine of Histone H3 at position 4 and triple-methylation of lysine of Histone H3 at position 27 in target genes indicates that said target stem cells have differentiation potential towards specific cell types indicated by the target genes.

Preferably, said target genes are selected from the group consisting of one or more pedigrees of sub-totipotent genes, triploblastic early differentiation genes, neural differentiation related genes, adipogenic genes, osteogenic genes, hematopoietic related genes or liver epithelial differentiation related genes, or comprise all differentiation related transcription factors of other pedigrees, wherein said totipotent genes include Oct4, Nanog, c-Myc, Sall4, Sox2, Klf4; ectoderm early differentiation related genes include Hoxa1, Gbx2, Six1 and Olig3; mesendoderm early differentiation related genes T, Pgdfrα, Eomes, Tbx6 and Mix11; mesoderm early differentiation related genes Kdr, Hand1, Gata4 and Mesp2; definitive endoderm early differentiation related genes Onecut1, Prox1, Foxa1, Foxa2, Sox7, Sox17, Pdx1 and Gsc, neural differentiation related genes include Tubb3, Nkx2-2, Sox1, Neurog1, Asc11, Brn2, Mytl1, Zic1, Neurog2, Hes1, Dlx1, Pax6, Tlx2, Msi1, Gfra1, Gfra3, Mapt, Nes, Olig2, Neurod1, Neurod2, adipogenic genes include C/EBPα, PPARγ, ERK5, GSK3α, GSK3β, C/EBPδ, C/EBPβ, osteogenic genes include RUNX2, BMP4, Smad5, TAZ, MSX2, DLX5, BMPR2, Wnt5a, hematopoietic related genes include c-Myb, EGR1, FOG1, SCL, E47, Ikaros, Gata1, BCL-6, liver epithelial differentiation related genes include Mxi11, Gsc, Sox17, Prox1, Hnf1β, Hnf6, E-cadherin, Foxa1, Foxa2, Snai1, Neurog2, Gfra2.

The fourth aspect of the present invention relates to use of histone modification states of sub-totipotent genes and/or differentiation related genes as epigenetic modification labels for predicting differentiation potential of stem cells, wherein the differentiation potential of stem cells is predicted by detecting the histone methylation modification states of said sub-totipotent genes and/or differentiation related genes.

Preferably, the differentiation stages of said cells are determined by detecting the histone methylation modification states of the transcription factors at specific pedigree differentiation stages and marker genes.

Preferably, differentiation specificity of cells towards target pedigree is determined by analyzing the changes in histone modification states of related genes, which initiate the differentiation of other non-target pedigrees.

Preferably, said histone methylation modification is triple-methylation of lysine of Histone H3 at position 4, or coexistence of triple-methylation of lysine of Histone H3 at position 4 and triple-methylation of lysine of Histone H3 at position 27.

Preferably, sub-totipotent genes and/or differentiation related genes are selected from the group consisting of one or more pedigrees of totipotent genes, triploblastic early differentiation genes, neural differentiation related genes, adipogenic genes, osteogenic genes, hematopoietic related genes or liver epithelial differentiation related genes, or comprise all differentiation related transcription factors of other pedigrees, wherein totipotent genes include Oct4, Nanog, c-Myc, Sall4, Sox2, Klf4; ectoderm early differentiation related genes include Hoxa1, Gbx2, Six1 and Olig3; mesendoderm early differentiation related genes T, Pgdfrα, Eomes, Tbx6 and Mix11; mesoderm early differentiation related genes Kdr, Hand1, Gata4 and Mesp2; definitive endoderm early differentiation related genes Onecut1, Prox1, Foxa1, Foxa2, Sox7, Sox17, Pdx1 and Gsc, neural differentiation related genes include Tubb3, Nkx2-2, Sox1, Neurog1, Asc11, Brn2, Mytl1, Zic1, Neurog2, Hes1, Dlx1, Pax6, Tlx2, Msi1, Gfra1, Gfra3, Mapt, Nes, Olig2, Neurod1, Neurod2, adipogenic genes include C/EBPα, PPARγ, ERK5, GSK3α, GSK3β, C/EBPδ, C/EBPβ, osteogenic genes include RUNX2, BMP4, Smad5, TAZ, MSX2, DLX5, BMPR2, Wnt5a, hematopoietic related genes include c-Myb, EGR1, FOG1, SCL, E47, Ikaros, Gata1, BCL-6, liver epithelial differentiation related genes include Mxi11, Gsc, Sox17, Prox1, Hnf1β, Hnf6, E-cadherin, Foxa1, Foxa2, Snai1, Neurog2, Gfra2.

Preferably, the histone methylation modification states of said sub-totipotent genes and/or differentiation related genes are detected by using ChIP-Seq or ChIP-PCR.

Preferably, different histone methylation states of said sub-totipotent genes and/or differentiation related genes represent different differentiation potentials of stem cells, primary histone methylation modifications of certain pedigree differentiation related genes being triple-methylation of lysine of Histone H3 at position 4 and coexistence of triple-methylation of lysine of Histone H3 at position 4 and triple-methylation of lysine of Histone H3 at position 27 indicate that such stem cells have differentiation potential towards this pedigree, when comparing two or more types of stem cells, those stem cells, having higher ratio of modified pedigree related genes as a whole, are more likely to differentiate towards said pedigree, wherein the modifications of the modified pedigree related genes are triple-methylation of lysine of Histone H3 at position 4 and coexistence of triple-methylation of lysine of Histone H3 at position 4 and triple-methylation of lysine of Histone H3 at position 27.

In other words, the present invention obtains all DNA from target stem cells with ChIP, wherein said DNA binds to antibodies specifically against the triple-methylated lysine of Histone H3 at position 4 and against the triple-methylated lysine of Histone H3 at position 27; and then the sequence information of said DNA is obtained through high-throughput sequencing; by aligning with genomic information, genome-wide histone modification profile of target stem cells is obtained, or histone modification state of certain gene is obtained by designing primers specific to certain gene. Wherein, the presence of triple-methylation of lysine of Histone H3 at position 4 (H3K4me3) or coexistence of triple-methylation of lysine of Histone H3 at position 4 (H3K4me3) and triple-methylation of lysine of Histone H3 at position 27 (H3K27me3) in target gene indicate that said target stem cell has differentiation potential towards specific cell type indicated by the target gene. If the primary histone methylation modifications of certain pedigree differentiation related genes are triple-methylation of lysine of Histone H3 at position 4 and coexistence of triple-methylation of lysine of Histone H3 at position 4 and triple-methylation of lysine of Histone H3 at position 27, it indicates that such stem cells have differentiation potential towards this pedigree. When comparing two or more types of stem cells, those stem cells, having higher ratio of modified pedigree differentiation related genes as a whole, are more likely to differentiate towards said pedigree. Wherein the modifications of the modified pedigree differentiation related genes are triple-methylation of lysine of Histone H3 at position 4 and coexistence of triple-methylation of lysine of Histone H3 at position 4 and triple-methylation of lysine of Histone H3 at position 27. Any genes, which indicate the sub-totipotent or pedigree differentiation of stem cells or stem cells having specific differentiation potential, can be used in the method according to the invention, including but not limited to one or more pedigrees of totipotent genes including Oct4, Nanog, c-Myc, Sall4, Sox2, Klf4; ectoderm early differentiation related genes including Hoxa1, Gbx2, Six1 and Olig3; mesendoderm early differentiation related genes T, Pgdfrα, Eomes, Tbx6 and Mix11; mesoderm early differentiation related genes Kdr, Hand1, Gata4 and Mesp2; definitive endoderm early differentiation related genes Onecut1, Prox1, Foxa1, Foxa2, Sox7, Sox17, Pdx1 and Gsc, neural differentiation related genes including Tubb3, Nkx2-2, Sox1, Neurog1, Ascl1, Brn2, Mytl1, Zic1, Neurog2, Hes1, Dlx1, Pax6, Tlx2, Msi1, Gfra1, Gfra3, Mapt, Nes, Olig2, Neurod1, Neurod2, adipogenic genes including C/EBPα, PPARγ, ERK5, GSK3α, GSK3β, C/EBPδ, C/EBPβ, osteogenic genes including Runx2, BMP4, Smad5, TAZ, MSX2, DLX5, BMPR2, Wnt5a, hematopoietic related genes including c-Myb, EGR1, FOG1, SCL, E47, Ikaros, Gata1, BCL-6, liver epithelial differentiation related genes including Mxi11, Gsc, Sox17, Prox1, Hnf1β, Hnf6, E-cadherin, Foxa1, Foxa2, Snail, Neurog2, Gfra2, and said gene comprises all differentiation related transcription factors of other pedigrees (Note: terminal differentiation marker genes such as AP2, LPL, c-Kit, ALP, OPN, CK8, CK18 etc. are not suitable to be candidate genes for predicting differentiation potential).

Namely, the present invention extracts mesenchymal stem cells from a variety of tissues such as fetal/adult fat, bone marrow and umbilical cord, obtains monoclonal cells through limiting dilution and further amplifies said monoclonal cells, and then obtains induced Flk1-positive MSC with epithelioid morphology by adding appropriate amounts of activin A and Wnt3a etc. factors at appropriate time, wherein said MSC does not leads to the formation of teratoma in vivo in mouse. RT-PCR, immunofluorescence stain and Western Blot assay detection show that such Flk1-positive MSC expresses definitive endoderm marker genes Foxa2, Sox17; mesendoderm marker genes Gsc, T, Eomes; mesoderm marker genes Kdr, Tbx6; ectoderm marker genes Sox1, Pax6 etc. Flk1$^+$ MSC is induced in vitro and is discovered that said Flk1$^+$ MSC can further differentiate into adipocyte, osteocyte, liver epithelial, glial cells, pancreatic stem/progenitor cells and other tissues derived from triploblastic multi-pedigrees.

Such a differentiation potential capable of differentiating into tissues and cells derived from triploblastic multi-pedigrees while incapable of developing into whole individual is referred as sub-totipotency by us, and sub-totipotent Flk1$^+$ MSC is referred as sub-totipotent stem cells. The obtaining of such sub-totipotent stem cells provides ideal seed cells for research and clinical application of regenerative and translational medicines.

After analyzing the histone modification states of stem cells having different differentiation potentials, it is found that different histone H3K4 and H3K27 triple-methylation modification states of sub-totipotent and pedigrees differentiation related genes in stem cells are closely associated with the differentiation potentials of stem cells, and thus can be used to predict the differentiation potentials of stem cells; in addition, when the differentiation of stem cells towards a specific pedigree is initiated, before the gene expression is changed, the histone modification states of differentiation related genes will be reconstituted, thereby histone methylation modification states of target pedigree relate genes are more active, whereas histone modifications which initiate other pedigree differentiation related genes are further inhibited or silenced. Thus, the differentiation stages and differentiation specificities during differentiations of stem cells towards a certain pedigree can be identified by analyzing the dynamic changes of histone methylation modification states of said pedigree and other non-target pedigrees differentiation related genes. When the expressions of related genes differentiated towards a certain pedigree are activated, cells at this moment become partially differentiated cells. Thus, if the expression levels of pedigree differentiation related genes are used to measure the differentiation potentials of stem cells, many stem cells origins having more primitive and more extensive differentiation potentials will be missed. While the changes of histone modifications are earlier than those of gene expressions, the presence of triple-methylation of K4, and the coexistence of triple-methylations of K4 and K27 of histone H3 allow the maintenance of these genes at very low expression level, namely in a state of "to be ready for" activation or inactivation. Such a histone modification state benefits the differentiation of stem cells towards different pedigrees according to the changes of micro-environment or external conditions. Therefore, the differences of histone modification states of differentiation related genes can be used as powerful indicators for predicting and evaluating the differentiation potentials of stem cells derived from different origins. Namely, in the present description, it is found that "histone methylation modification states of sub-totipotent and differentiation related genes in stem cells are closely associated with the differentiation potentials of stem cells, thus the differentiation potentials of stem cells can be predicted by detecting the histone methylation modification states of sub-totipotent genes and differentiation related genes in said stem cells. Also, the histone methylation modification states of certain sub-totipotent genes and differentiation related genes can be used as labels for predicting the differentiation potentials of stem cells derived from certain origins. Such a method for predicting the differentiation potential of stem cells needs only to detect histone methylation states of sub-totipotent genes and differentiation related genes with ChIP-Seq or ChIP-PCR technology, does not need to perform differentiations of stem cells towards multi-pedigrees by induction. As seen, this greatly saves time, labor and reagent consumptions. Therefore, histone methylation modification state has vital clinical application value in predicting the differentiation potential of stem cells.

Utilizing the method of present application, differentiation state and differentiation potential of a certain stem cell can also be accurately determined by analyzing the histone methylation states of sub-totipotent genes and differentiation related genes, thereby crucial clinical instruction can be provided in order to ensure the proper clinical application of said stem cells.

DETAILED DESCRIPTION

Figure 1:
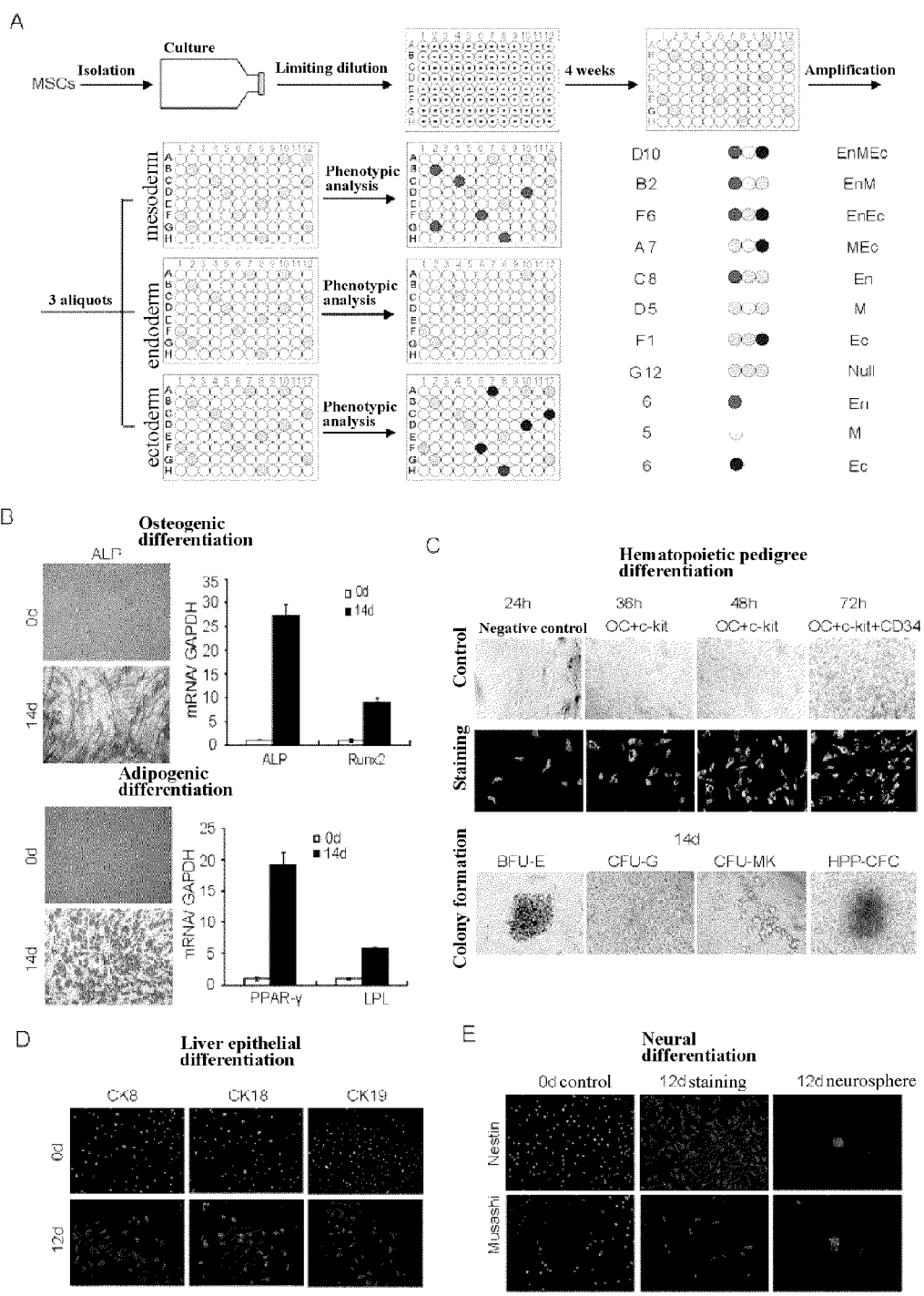
FIG. 1 shows the differentiation potential of Flk1$^+$ MSC. (A) monoclonal-derived aMSCs obtained with limiting dilutions, (B) Differentiations of Flk1$^+$ MSC towards adipogenic and osteogenic pedigrees, (C) Hematopoietic differentiation of Flk1$^+$ MSC and the identification thereof (OC: Osteocalcin, BFU-E: burst forming unit-erythroid, CFU-G: colony forming unit-granulocyte, CFU-MK: colony forming unit-megakaryocyte, HPP-CFC: high proliferative potential-colony forming unit), (D) Liver epithelial differentiation of Flk1$^+$ MSC and the identification thereof, (E) Neural differentiation of Flk1$^+$ MSC and the identification thereof.

The invention will be further illustrated by the following non-limiting examples. Various modifications of the invention will be apparent to those skilled in the art without departing from the spirit of the invention, and such modifications are intended to be within the scope of the invention.

Unless otherwise indicated, the following experimental methods are conventional methods. Unless otherwise indicated, the experimental materials used can be obtained commercially.

EXAMPLES

Example 1

Obtaining of Flk1$^+$ MSC and the Examination of Differentiation Potential Thereof In order to evaluate the clinical application value of Flk1$^+$ MSC, we examine the differentiation potential of Flk1$^+$ MSC at first.

Adult fat samples are collected from Plastic Surgery Hospital CAMS, adult bone marrow samples are collected from 307 Hospital of PLA. All samples are collected with signed informed consent.

Isolation of adult Adipose Mesenchymal Stem Cells (aMSCs):

Adult adipose tissue is obtained from patients in liposuction surgery (Plastic Surgery Hospital, CAMS) with informed consent signed by the donors. All donors are 25-35 year-old healthy women. aMSCs are isolated from adipose tissue by using the method described by Zuk et al [20], though modified slightly. The process is summarized as follows: the adipose tissue collected by liposuction is washed with D-Hanks in order to remove blood cells and anesthetics, and is digested for 1 h with 0.2% type II collagenase, and then is washed with D-Hanks for twice to remove the collagenase. Cells are collected by centrifugation and inoculated into culture solution (containing 58% DMEM/F12+40% MCDB-201, 5% fetal calf serum (FCS), 10 ng/ml EGF, 10 ng/ml PDGF, 1× Insulin-Transferrin-Selenium (ITS), 1× linoleic acid-bovine serum albumin (LA-BSA), 50 μM beta-mercaptoethanol, 2 mM L-glutamine, 100 μg/ml penicillin and 100 U/ml streptomycin sulfate) at a density of 2×10$^6$/ml, and cultivated at 37° C. in 5% $CO_2$, 95% humidity incubator. The medium is changed after 2 days, the non-adherent cells are removed, and then half of the medium is changed every 3 days. The cells are conventionally digested with 0.25% trypsin (Gibco) when 70%~80% confluence is reached; the cells are passaged in a ratio of 1:3.

Isolation of adult Bone Marrow Mesenchymal Stem Cells (bMSCs): [0063](1) 5-10 ml bone marrow is collected aseptically from healthy donors and placed into sterile heparin tubes.

(2) The bone marrow is appropriately diluted with D-Hanks solution in a sterile centrifuge tube and then the bone marrow cells are counted, the concentration of bone marrow cells is adjusted to 1×10$^7$/ml.

(3) Both of lymphocyte separation solution allowed to reach room temperature and bone marrow cell suspension described above are added into a new centrifuge tube at a ratio of 1:1, the manipulation of the addition shall be careful enough to avoid the disruption of interface.

(4) Before loaded into table centrifuge at room temperature, the centrifuge tubes shall be balanced, and the samples are centrifuged at 20° C. at 1800 rpm for 20 min Centrifuge tubes are taken out of centrifuge and used to carefully extract the white membrane layer under aseptic conditions, the mononuclear cells are obtained and washed with D-Hanks solution twice followed by counting.

(5) The mononuclear cells mentioned above are inoculated into 25 cm² culture flask at a density of 2×10⁶/ml, cell culture system is culture solution containing 58% DMEM/F12+40% MCDB-201, 2% fetal calf serum (FCS), 10 ng/ml EGF, 10 ng/ml PDGF, 1× Insulin-Transferrin-Selenium (ITS), 1× linoleic acid-bovine serum albumin (LA-BSA), 50 µM beta-mercaptoethanol, 2 mM L-glutamine, 100 µg/ml penicillin and 100 U/ml streptomycin sulfate, and cells are cultivated at 37° C. in 5%, $CO_2$ 95% humidity incubator.

(6) The suspended cells are removed 24 h later, and the culture is supplemented with medium, and the medium is changed every 3 days. The cells are digested with 0.05% trypsin-0.01% EDTA when 70%.about.80% confluences are reached, and then the cells are passaged. Mesenchymal stem cells of generations 1-2 are frozen and stored in a liquid nitrogen container.

By limiting dilution, aMSCs and bMSCs are inoculated onto wells of 96-well plate at a density of 1 cell/well. Three weeks later, grown monoclones can be observed in about 24.55%.+−0.0.66% wells. These monoclones are further proliferated and thereafter are used as seed cells, cells are cultivated for 4-6 h until complete adherence, and then No. 1 inducing medium (20 ng/ml activin A+200 ng/ml wnt3a+ 20% FBS+HG-DMEM) is added and the induction is maintained for 1 day, the medium is changed into No. 2 inducing medium (20 ng/ml activin A+100 µM RA+20% FBS+HG-DMEM) and induction is maintained for another 4 days, Flk1⁺ MSCs are harvested. The resulting Flk1⁺ MSCs having epithelioid morphology are subjected to RT-PCR detection, immunofluorescence staining detection (Foxa2, Sox17, Kdr, Tbx6, Eomes, Gsc, T, Sox1, Pax6 are detected) and Western Blot detection (Foxa2, Sox17, T, Gsc, Epcam, Vimentin are detected). The results suggest that the resulting Flk1⁺ MSCs have important gene phenotype markers (definitive endoderm markers Foxa2, Sox17; mesendoderm markers Gsc, T, Eomes; mesoderm markers Kdr, Tbx6; ectoderm markers Sox1, Pax6) which indicate the differentiation potentials towards three germ layers, and have high inducing efficiency (the efficiency of Foxa2, Sox17 positive definitive endoderm cells are 90% or more). The results are shown in FIGS. 8-11.

Six aliquots of the resulting Flk1⁺ MSC are induced towards liver epithelial, neural, hematopoietic, adipogenic and osteogenic pedigrees, respectively. Another aliquot which is allowed to continue to proliferate is used as control for other pedigrees (FIG. 1A). After 14 days of induction, oil droplets can be observed within the cytoplasm of adipogenic induced group cells under light microscope, positive rate of Oil Red 0 staining is up to 80%, high expressions of adipogenic marker genes AP2 and LPL are shown in real-time quantitative PCR analysis (FIG. 1B); in the group of osteogenic induction, the ALP and Alizarin red staining positive rate is up to 65%, significantly up-regulated expressions of osteogenic marker genes ALP and OPN are shown in real-time quantitative PCR analysis when compared with that before induction (FIG. 1B). On the third day of hematopoietic induction of Flk1⁺ MSC, hematopoietic related marker molecules Osteocalcin (OC), c-Kit and CD34 staining is positive. On the $14^{th}$ day of induction, the formation of various hematopoietic colonies can be observed, such as BFU-E (burst forming unit-erythroid), CFU-G (colony forming unit-granulocyte), CFU-MK (colony forming unit-megakaryocyte) and HPP-CFC (high proliferative potential-colony forming unit) and the like (FIG. 1C). On the $21^{st}$ day of induction, in the group of liver epithelial induction, cells present CK8, CK18 and CK19 positive in immunohistochemical detection (FIG. 1D). On the $12^{nd}$ day of induction, in the group of neural induction, cells present Nestin and Musashi positive in immunohistochemical detection (FIG. 1E). The above results indicate that Flk1⁺ MSCs, under certain inducing conditions, are capable of differentiating towards multi-pedigrees derived from different germ layers, such as liver epithelial, neural, hematopoietic and adipogenic and osteogenic pedigrees and the like.

Example 2

The Relationship Between Different Histone H3K4me3 and H3K27me3 Modification States of Differentiation Related Genes and Differentiation Potentials of Stem Cells Flk1⁺ MSCs have been proved to be capable of differentiating towards multi-pedigrees from different germ layers, such as liver epithelial, neural, hematopoietic, adipogenic and osteogenic pedigrees and the like, and then we further obtain the genome-wide histone methylation modification profile of Flk1⁺ MSCs by using the combination of ChIP detection technique and bioinformatics analysis (ChIP-Seq).

The ChIP assays of H3K4me3 (Abcam 8580) and H3K27me3 (Upstate 07-449) are performed according to the standard protocol of EZ ChIP™ kit (Millipore).

The basic procedures are as follows:
1. The Preparation of Chromatin Sample and Immunoselection (1) Cells are cultivated, and fixed with 1% formaldehyde at room temperature for 10 min in order to allow the cross-linking between proteins and DNA, (2) Cells are treated by lysis and sonication (Branson 250D sonicator), the length of chromatin fragment is within the range of 200-1000 bp, (3) Immunoselection is performed using specific antibodies, H3K4me3 (Abcam 8580) and H3K27me3 (Upstate 07-449).

2. Purification and Detection of DNA (4) DNA is isolated and purified, proteins are removed, and cross-linking between proteins and DNA is removed by incubation at 65° C., (5) Specific primers are designed for target genes, DNA sequences are identified by PCR or real-time PCR.

Positive control:
Anti-RNA polymerase II, it binds to all gene promoter regions that activate transcription.

Negative control: Common IgG against origins from identical species.

Primer control: promoter region of GAPDH gene.
3. Immunoprecipitation (IP) Crosslink Preparation before beginning: protease inhibitor Cocktail II is dissolved at room temperature, said reagent contains DMSO, which is in solid state below 18.4° C.

(6) Dilution buffer containing protease inhibitor is prepared and placed on ice.

Each IP needs 900 µl Dilution Buffer plus 4.5 µl PI cocktail.

Samples include positive control (anti-RNA Polymerase II), negative control (common IgG of the same species) and target proteins. It is recommended that the origin species of negative control IgG is identical to that from which the antibodies of target proteins are derived.

(7) The prepared EP tube containing 100 μl product is placed on ice and subjected to ChIP. The frozen samples shall be allowed to thaw in advance.

If a chromatin product will be subjected to multiple IP, the product can be held in a large tube (EP tube capable of holding 1.1 ml solution). Each 100 μl product contains chromatin derived from about $2\times10^6$ cells.

(8) 900 μl Dilution Buffer containing PI cocktail is added into each 100 μl chromatin product.

In the cases involving multiple IP, corresponding amount of Dilution Buffer can be added.

(9) 60 μl Protein G Agarose is added into each IP.

Protein G Agarose is in the form of 50% slurry, which shall be gently mixed before use.

This step is referred as "preclear" of chromatin, and the aim thereof is to remove those proteins and DNA that non-specifically bind to Protein G Agarose.

In the cases involving pooling treatment of many aliquots, corresponding amount of Protein G Agarose can be added.

(10) Incubation is performed at 4° C. for 1 hour with rotation.

(11) Agarose is precipitated by centrifugation at 3000-5000 g for 1 min.

Centrifugation of Protein G Agarose at high-speed shall be avoided, since if the centrifugal force is too large, the beads will be crushed or deformed.

(12) 10 μl (1%) supernatant is taken as Input, and kept at 4° C. before being used for step 5.

In the cases involving many parallel treatments, each of 1% chromatin samples are used as Input.

(13) 1 ml supernatant is collected and transferred to a new EP tube.

(14) Antibody used for immunoprecipitation is added into supernatant. 1.0 μg anti-RNA polymerase antibody is added into positive control tube.

1.0 μg common IgG from the same species is added into negative control tube.

1-10 μg antibody is added into the tube to be tested. The amount of antibody added can be based on previous experience.

(15) Incubation is performed overnight at 4° C. with rotation. Depending on many factors such as antibodies, target genes and cell types, the IP incubation time can be shortened.

(16) 60 μl Protein G Agarose is added, incubation is performed at 4° C. for 1 hour with rotation.

(17) Agarose is precipitated by centrifugation at 3000-5000 g for 1 min, and the supernatant is removed.

(18) Protein G Agarose/chromatin complex is washed with 1 ml following solutions in turn. After suspension, complex is incubated with rotation for 3-5 min, and centrifuged at low speed 3000-5000 g for 1 min, and then the supernatant is removed.
  a. Low salt immune Complex Wash Buffer, once;
  b. High Salt Immune Complex Wash Buffer, once;
  c. LiCl Immune Complex Wash Buffer, once;
  d. TE buffer, twice. 4. Protein/DNA complex is eluted.

Preparation before beginning:

1M $NaHCO_3$ is placed at room temperature. Limit amount of precipitation can be observed. The precipitation will be dissolved when room temperature is reached. 1M $NaHCO_3$ can be vortexed.

65° C. water bath is prepared.

(1) Elution buffer is prepared for each IP tube including Input tube (see Section 3, Step 7). Each tube needs 200 μl Elution buffer. The preparation method: 10 μl 20% SDS, 20 μl 1M $NaHCO_3$, supplemented with 170 μl $H_2O$.

(2) Alternatively, buffer can be prepared together in a big tube, for example in the case involving 10 IP tubes, 105 μl 20% SDS, 210 μl 1M $NaHCO_3$, supplemented with 1.785 μl $H_2O$.

(3) 200 μl Elution buffer is added into Input tube and kept at room temperature before being processed in step 5.

(4) 100 μl Elution buffer is added into antibody/agarose complex in each tube, and mixed with gentle flick.

(5) Incubation is performed at room temperature for 15 min.

(6) Agarose is precipitated by centrifugation at 3000-5000 g for 1 min, and the supernatant is collected into a new EP tube.

(7) Steps (4) to (6) are repeated, eluate is pooled to obtain a total volume of 200 μl. 5. Protein/DNA is de-crosslinked in order to obtain free DNA (1) 8 μl 5M NaCl is added into all tubes (including IPs and Inputs), tubes are incubated at 65° C. for 4-5 hours or overnight to remove the protein/DNA crosslink. After this, samples can be stored at −20° C. Subsequent experiments are performed on the next day.

(2) 1 μl RNase A is added into all tubes, incubation is performed at 37° C. for 30 min.

(3) 4 μl 0.5M EDTA, 8 μl 1M Tris-HCl and 1 μl proteinase K are added, incubation is performed at 45° C. for 1-2 hours. 6. DNA is purified with Spin Columns (1) A collection tube and an isolation tube are prepared for each sample. Spin Column is put into collection tube.

(2) 1 ml Bind Reagent A is added into 200 μl DNA sample, and then mixed.

The volume of Bind Reagent A added is 5 folds of that of sample.

Precipitation can be observed but does not affect this step.

(3) The mixture of 600 μl sample/Bind Reagent A is added into Spin filter of collection tube.

(4) Centrifuged at >10,000 g for 30 seconds.

(5) Spin filter is removed; the liquid in collection tube is discarded, while the collection tube is maintained.

If precipitation is observed in step 2, visible precipitation can be observed at the bottom of the tube of present step, which does not affect this test.

(6) Spin filter is replaced into the collection tube.

(7) 600 μl of the mixture of sample/Bind Reagent A in step 2 is added into Spin filter, and steps (4) to (6) are repeated.

(8) 500 μl Wash Reagent B is added into Spin filters of collection tube.

(9) The tube is centrifuged at >10,000 g for 30 seconds.

(10) Spin filter is removed from the collection tube, the liquid in collection tube is discarded, while the collection tube is maintained.

(11) Spin filter is replaced into the collection tube.

(12) The tube is centrifuged at >10,000 g for 30 seconds.

(13) The collection tube and the liquid are discarded.

(14) Spin filter is put into the collection tube.

(15) 50 μl Elution Buffer C is directly added into the center of the white Spin membrane.

(16) The tube is centrifuged at >10,000 g for 30 seconds.

(17) Spin filter is discarded. The elution is purified DNA which can be directly used for analysis or stored at −20° C. 7. Control PCR Caution: all the pipettes and tips used in this section should be properly handled in order to avoid contamination.

(1) 0.2 ml PCR tubes are marked and placed on ice.

At least four DNA samples are subjected to PCR analysis using control primers when using the kit. IP primers of positive and negative control antibodies are included, Input and DNA-free empty tube are served as control tubes for the presence or absence of DNA contamination. Control primers are specific to human GAPDH gene. As for other objects, it is recommended that specific primers can be designed by the user based on experiences.

(2) 2 μl sample is added into each tube and replaced onto the ice.

(3) Proper amount of reagent is added into each reaction tube in accordance with table 1, water and Taq polymerase etc. are added in turn. It is recommended that hot start Taq polymerase can be used. If hot start Taq polymerase is not used, addition of Taq polymerase after initial denaturation step is recommended. 8. All DNA samples binding to H3K4me3 and H3K27me3 antibodies obtained from ChIP are subjected to high-throughput sequencing, i.e. ChIP-Seq technique. 9. Target gene-specific primers are designed. All DNA samples binding to H3K4me3 and/H3K27me3 antibodies obtained from ChIP are used as substrates and subjected to PCR reactions, which is referred as ChIP-PCR technique.

Flk1$^+$ MSC genome-wide histone K4 and K27 site methylation modification state is obtained after calibrated according to human genome database (Hg 18). Stem cells with different differentiation potentials, such as ESC, Flk1$^+$ MSCs, HSCs (hematopoietic stem cells) and HPCs (hematopoietic progenitor cells) and the like are selected by us and used as the objects of study [21, 22]. Histone methylation modification states of sub-totipotent genes and liver epithelial, neural, hematopoietic, adipogenic and osteogenic pedigree related genes in these stem cells are analyzed and compared.

Figure 2:
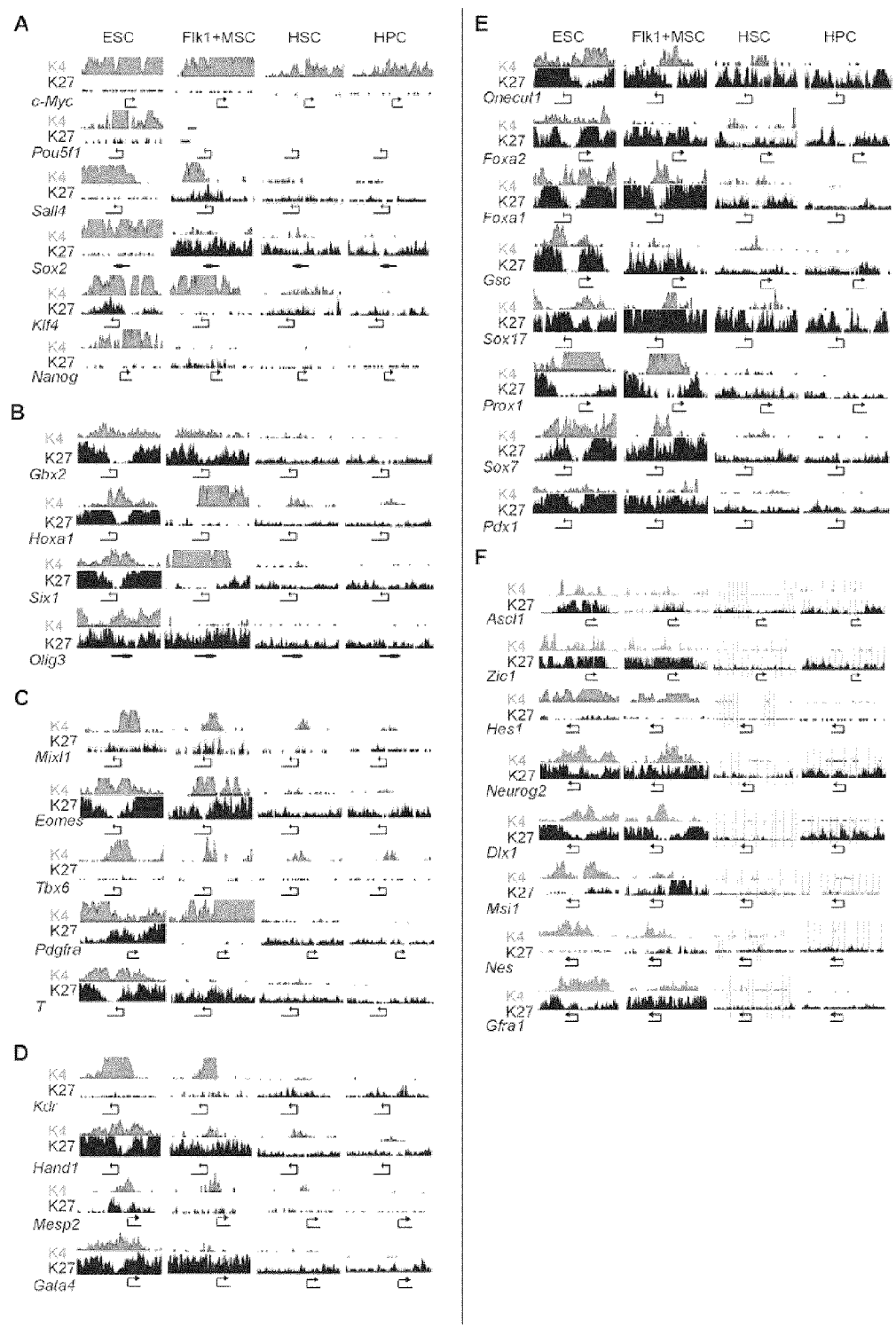
FIG. 2 shows the differences of histone methylation modification profiles among totipotential genes, triploblastic early differentiation related genes and neural differentiation related genes of different grades of stem cells. (A) Histone methylation modification profile of totipotency related genes, (B) Histone methylation modification profile of ectoderm differentiation related genes, (C) Histone methylation modification profile of mesendoderm differentiation related genes, (D) Histone methylation modification profile of mesoderm differentiation related genes, (E) Histone methylation modification profile of definitive endoderm differentiation related genes, (F) Histone methylation modification profile of neural differentiation related genes.

Based on the analysis of histone methylation modification of sub-totipotent genes, it is found that all of Oct4, Nanog, c-Myc, Sall4 and Sox2 in ESCs are H3K4me3 activating modified, Klf4 has bivalent modification of coexistence of both H3K4me3 and H3K27me3; c-Myc and Klf4 in Flk1$^+$ MSCs are H3K4me3 activating modified, Sall4 and Sox2 are bivalently modified, Oct4 and Nanog show substantially absence of modification signals; in HSCs and HPCs, all sub-totipotent genes are H3K27me3 inhibiting modified or absence of modification, except that c-Myc which is considered to be closely associated with cell cycle is activating modified (FIG. 2A). Histone methylation modifications of ectoderm early differentiation related genes including Hoxa1, Gbx2, Six1 and Olig3; mesendoderm early differentiation related genes T, Pgdfrα, Eomes, Tbx6 and Mixl11; mesoderm early differentiation related genes Kdr, Hand1, Gata4 and Mesp2, definitive endoderm early differentiation related genes Onecut1, Prox1, Foxa1, Foxa2, Sox7 Sox17, Pdx1 and Gsc in ESCs and Flk1$^+$ MSCs are very similar, most of the modifications are K4 activating or bivalent modification state (FIGS. 2B, 2C, 2D and 2E). Neural differentiation related genes reported in currently literatures mainly include 22 transcription factors such as Brn2, Myt1L, Zic1, Neurog2, Hes1, Dlx1, Pax6, Tlx2, Msi1, Gfra1, Gfra3, Mapt, Nes and Olig2 etc. [23-25]. ChIP-Seq analysis data suggest that 17 genes in ESCs exhibit H3K4me3 modification or bivalent modification states; the analysis results in Flk1$^+$ MSCs are similar to that in ESCs; in addition, the analysis results show that all histone modification states of 3 neural differentiation initiation related genes Nes, Msi1 and Hes1 in ESCs and Flk1$^+$ MSCs are H3K4me3 activating state; whereas in HSCs and HPCs, some of these genes exhibit H3K27me3 inhibiting modification, the modification signals of remaining genes are not detected (FIG. 2F).

Figure 3:
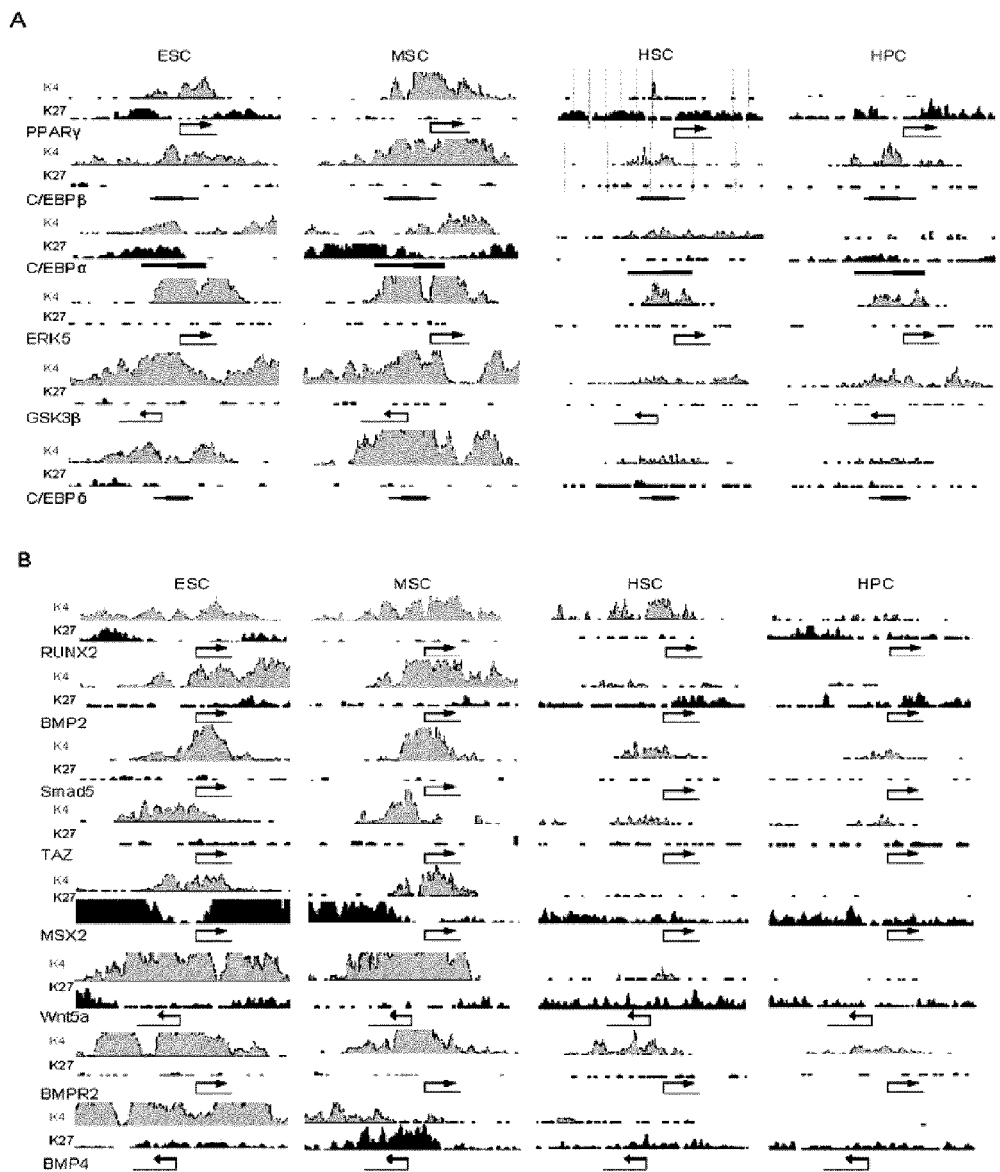
FIG. 3 shows the differences of methylation modification profiles between adipogenic (A) and osteogenic (B) differentiation related genes in different stem cells.

Next, the inventor compares the histone modification states of mesoderm related pedigrees adipogenic, osteogenic and hematopoietic differentiation related genes in the stem cells mentioned above. The results show that the key adipogenic transcription factors C/EBPα and PPARγ in Flk1$^+$ MSCs exhibit H3K4me3 activating modification, whereas in ESCs exhibit bivalent modification; the histone modifications of their upstream regulation factors ERK5, BMP2, GSK3α, GSK3β, C/EBPδ and C/EBPβ in the ESCs and Flk1$^+$ MSCs are similar. Similarly, the histone modifications of these genes in HSCs and HPCs are also H3K27me3 inhibiting state or absent of modification (FIG. 3A). Similar results are obtained in histone methylation analysis of osteogenesis related genes, that is, key osteogenic transcription factor RUNX2 in Flk1$^+$ MSCs is H3K4me3 activating modified, whereas in ESCs is bivalently modified; the Runx2 upstream regulation factors BMP2, BMP4, Smad5, TAZ, MSX2, DLX5 and Wnt5a exhibit similar histone methylation modifications in two types of cells (FIG. 3B). The analysis of histone methylation modifications of hematopoietic differentiation related genes c-Myb, EGR1, FOG1 (ZFPM1), SCL (TAL1), E47 (TCF3), Ikaros (IKZF1), Gata1 and BCL-6 etc. show that c-Myb, EGR1, E47 and BCL-6 exhibit H3K4me3 activating modification state in 4 types of stem/progenitor cells; FOG1, SCL and Ikaros in ESCs and Flk1$^+$ MSCs exhibit bivalent modification, whereas in HSCs and HPCs exhibit H3K4me3 activating modification; Gata1 in ESCs and Flk1$^+$ MSCs exhibits inhibiting modification or absence of modification, whereas in HSCs and HPCs exhibits H3K4me3 activating modification (FIG. 4A).

Figure 4:
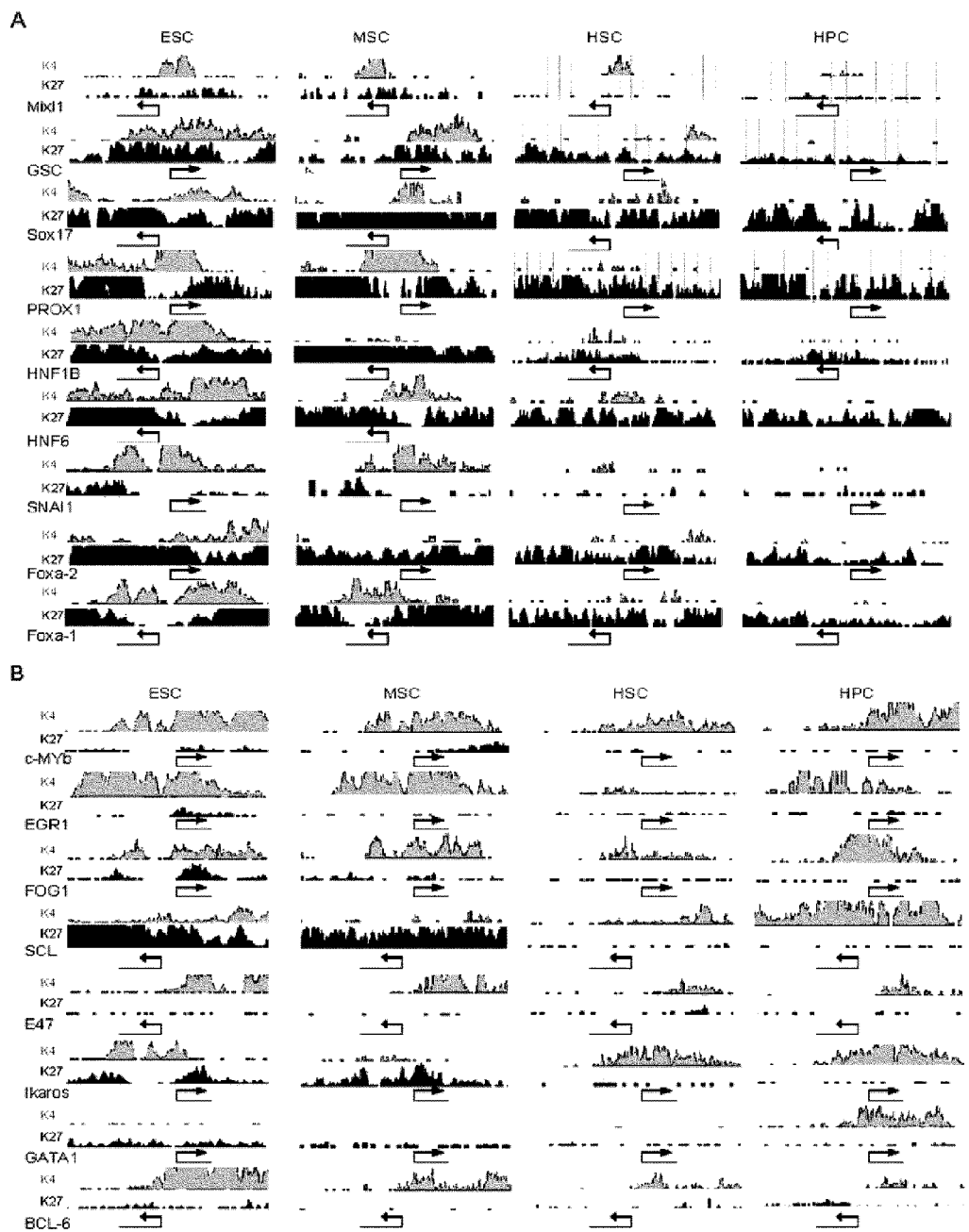
FIG. 4 shows the differences of methylation modification profiles between liver epithelial (A) and hematopoietic (B) differentiation related genes in different stem cells.

Further analysis of endoderm liver epithelial pedigree related genes shows that all of Mxi11 Gsc, Sox17, Prox1, Hnf1β, Hnf6, E-cadherin, Foxa1 and Foxa2 etc. in ESCs exhibit activating or bivalent modification; wherein Mxi11, Gsc, Sox17, Hnf6, Prox1 and Foxa1 in Flk1$^+$ MSCs also exhibit activating or bivalent modification, Foxa2 which shares similar function with that of Foxa1 exhibits H3K27me3 inhibiting modification; the upstream regulation factor of epithelial marker molecule E-cadherin (Snail) exhibits activation signal; all of the histones of liver epithelial differentiation related genes in HSCs exhibit H3K27me3 inhibiting signal or absence of modification, except that Mxi11 exhibits weak activating modification signal; whereas in HPCs, every liver gene exhibits H3K27me3 inhibiting signal or absence of modification (FIG. 4B).

The analysis and comparison of genome-wide histone modifications show that, in six genes in ESCs, five genes exhibit activating modification and one gene exhibits bivalent modification, the histone methylation states of key transcription factors involving in the differentiations towards each germ layer are H3K4me3 activating or bivalent modification in general; in six genes in Flk1$^+$ MSC, two genes exhibit activating modification, the other four exhibit bivalent modification. Almost all hematopoietic differentiation related genes in HSCs mainly exhibit activating modification, while other pedigrees related genes mainly exhibit H3K27me3 or absence of modification signal. Other pedigrees related genes in HPCs exhibit H3K27me3 inhibiting modification or absence of modification signal, whereas all hematopoietic differentiation related genes exhibit H3K4me3 activating modification, and the activating signals thereof are stronger than those shown in HSCs; hematopoietic pedigree directed differentiation factor Gata1 in ESCs, Flk1$^+$ MSCs and HSCs exhibits inhibiting modification or absence of modification, whereas in hematopoietic progenitor cells exhibits H3K4me3 activating modification. It is supposed that it is actively modified when the pluripotent stem cells are hematopoietically differentiated to hematopoietic progenitor cell stage, so as to allow the further directed differentiation of hematopoietic pedigree. Overall, from ESCs, Flk1+ MSCs, HSCs to HPCs, the histone methylation modification states of hematopoietic differentiation related genes show such a process that H3K27me3 inhibiting modification gradually disappears and H3K4me3 activating modification signal gradually increases, however other non-hematopoietic related pedigrees show such a process that activating modification gradually decreases and inhibiting modification signals (including H3K27me3 and absence of modification, both lead to gene silencing) increases. Previous research proves that ESCs have differentiation totipotency towards all pedigrees of all germ layers. However, the experiments of the present invention indicate that Flk1+ MSC has differentiation sub-totipotency towards multi-pedigrees of multi-germ layers such as liver epithelial, neural, hematopoietic, vascular endothelial, adipogenic and osteogenic pedigrees and the like. HSCs only exhibit differentiation potential towards hematopoiesis related pedigrees, and HPCs are cells that are more directed towards differentiation of hematopoietic pedigrees than HSCs. The analysis results of different histone modification states of every pedigree differentiation related gene in HSCs and HPCs and the different differentiation potentials of these stem cells have indicated that, along with the decreasing of pluripotent level and the changes in histone methylation modification states, stem cells gradually lose their differentiation totipotency (ESCs) and develop into sub-totipotent cells (Flk1+ MSCs) or cells with differentiation potential towards only one germ layer (HSCs) or even only one pedigree (progenitor cells). Histone H3K4me3 and H3K27me3 modification states of differentiation related genes are closely associated with differentiation potentials of stem cells, so they can be used as epigenetic modification labels for predicting the differentiation potentials of stem cells.

Example 3

Figure 5:
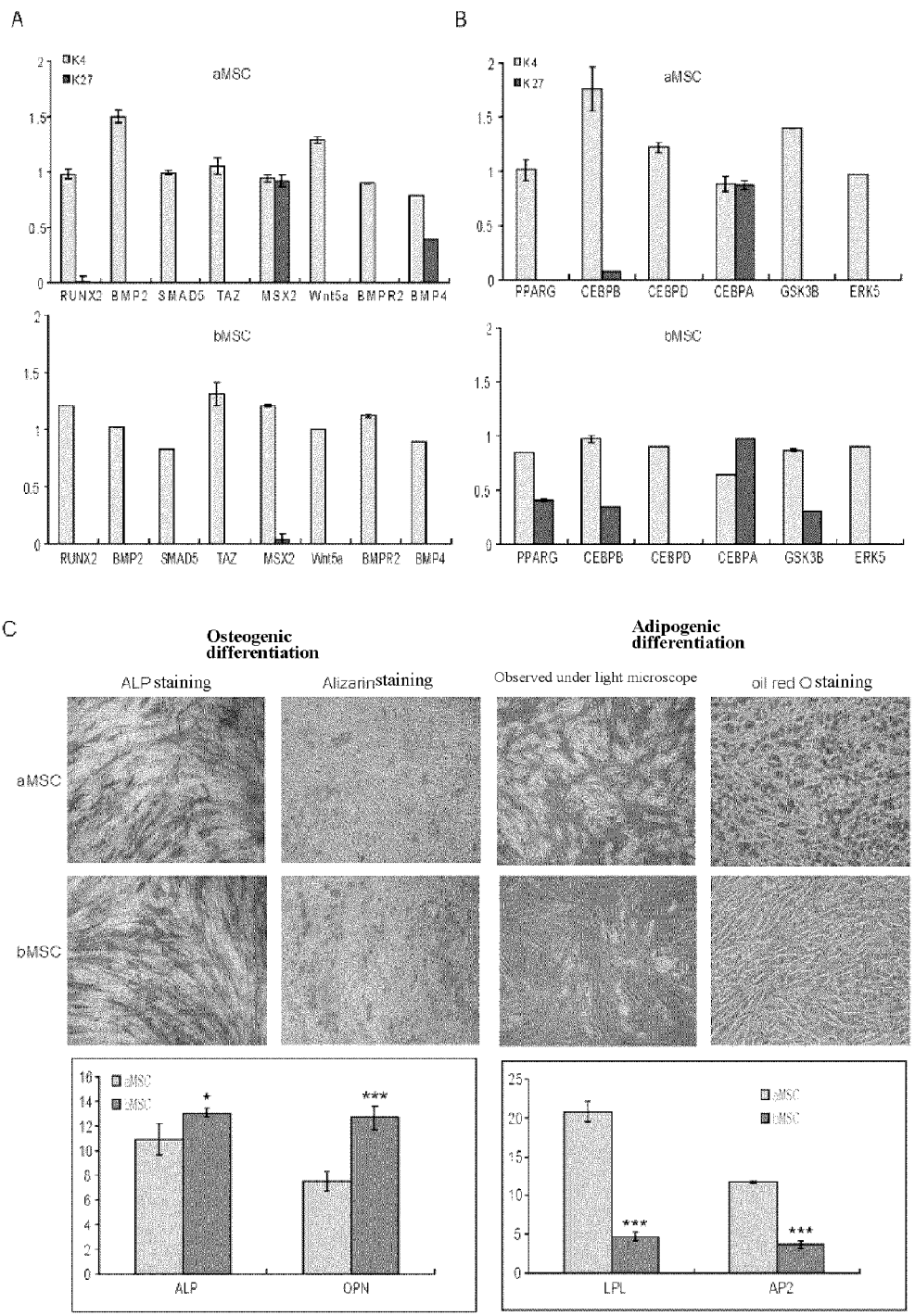
FIG. 5 shows the comparisons of histone methylation modifications and differentiation potentials of adipogenic/osteogenic differentiation related genes of aMSC and bMSC. (A) Histone methylation modification states of osteogenesis related genes in aMSC and bMSC with ChIP-PCR analysis, (B) Histone methylation modification states of adipogenesis related genes in aMSC and bMSC with ChIP-PCR analysis, (C) Comparison of differentiation potentials of aMSC and bMSC towards osteogenic and adipogenic pedigrees.
Figure 6:
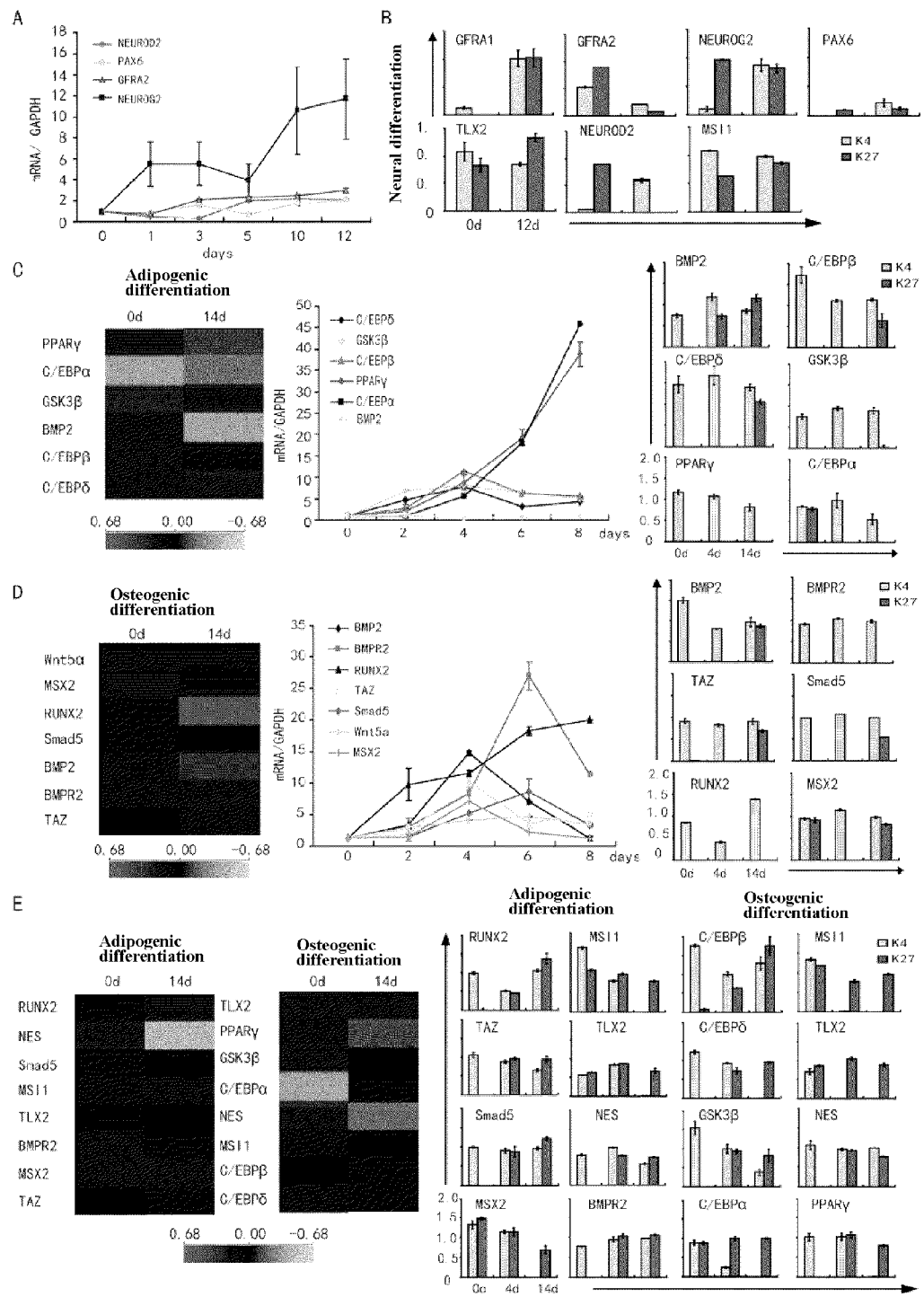
FIG. 6 shows the dynamic changes of histone methylation modification of neural, adipogenic and osteogenic differentiation related genes. (A) Determination of expressions of related genes before and after neural differentiations by real-time PCR, (B) Determination of histone methylation states of related genes before and after neural differentiations by ChIP-PCR, (C) Determination of expressions and histone methylation states of related genes before and after adipogenic differentiations by real-time PCR and gene chip analysis, (D) Determination of expressions and histone methylation states of related genes before and after osteogenic differentiations by real-time PCR and gene chip analysis, (E) Determination of expressions and histone methylation states of other pedigree related genes during adipogenic differentiation or osteogenic differentiation by real-time PCR and gene chip analysis.
Figure 7:
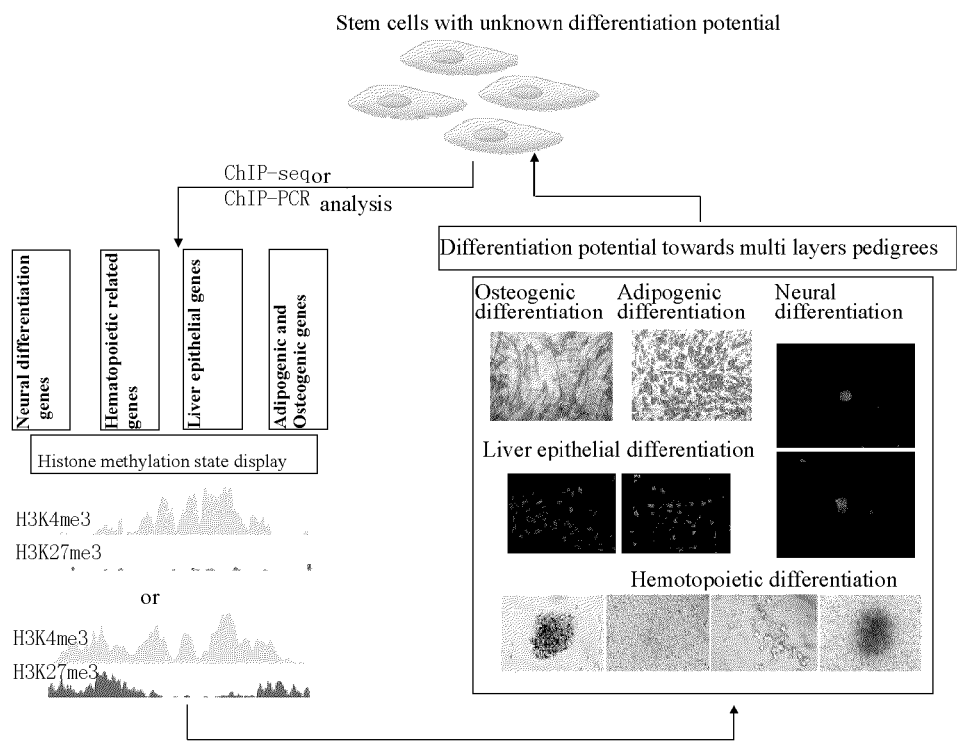
FIG. 7 is a schematic diagram showing the prediction of differentiation potential of stem cells with histone methylation modification state.
Figure 8:
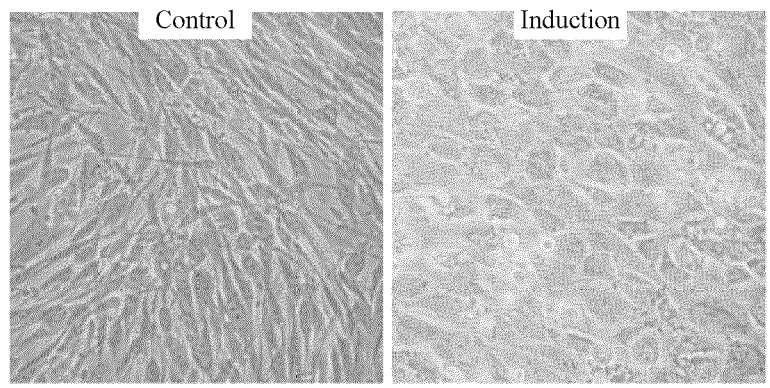
FIG. 8 shows the morphological alternations before and after induction: L: cells are arranged in fusiform before induction, R: cells are densely arranged in cobble-like after induction.
Figure 9:
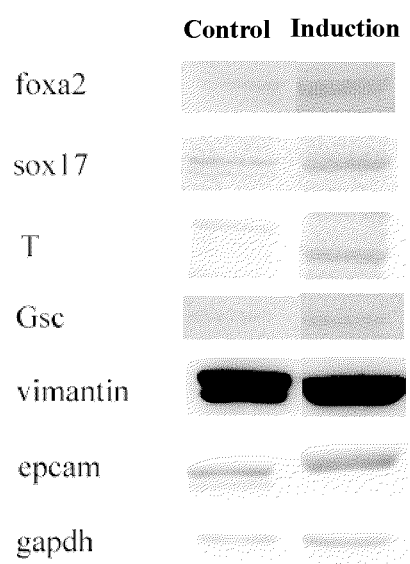
FIG. 9 shows the results of RT-PCR detection before and after induction. From left to right: the gene expressions of definitive endoderm markers foxa2, Gsc, T, Eomes (P<0.05) and ectoderm markers Sox1, Pax6 (P<0.05) are up-regulated, while the gene expressions of mesoderm markers Kdr, Tbx6 do not change significantly (P>0.05).
Figure 10:
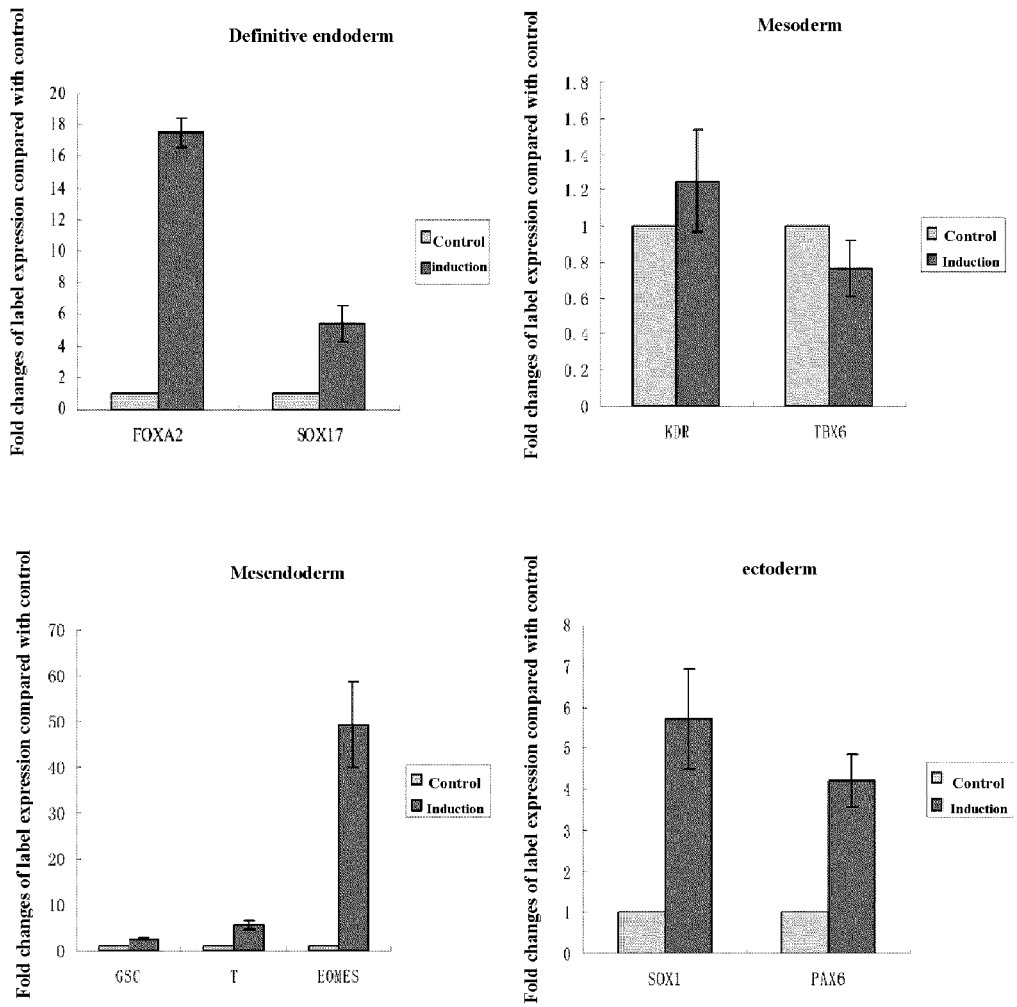
FIG. 10 shows Western Blot analysis of cells performed before and after induction: the expression abundances of endoderm markers Foxa2, sox17 and mesendoderm markers T, Gsc significantly increase, the expression abundance of epithelial marker Epcam also increases, while the expression abundance of mesenchymal cell marker Vimentin does not change significantly, after induction.
Figure 11:
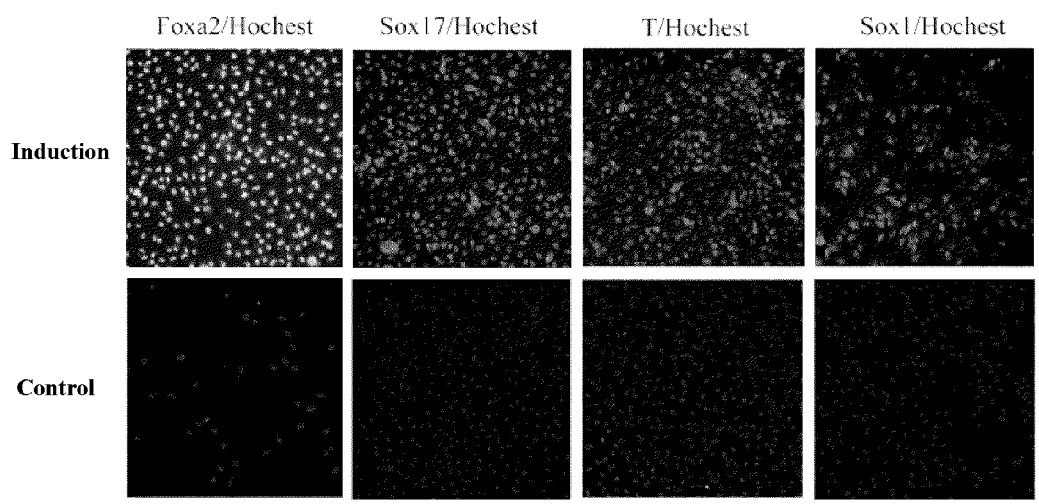
FIG. 11 shows immunofluorescence cell staining analysis of cells performed before and after induction: when compared with non-induced cells, endoderm markers Foxa2, sox17 positive cells reach 90% or more, mesendoderm marker T positive cells reach 70% or more, ectoderm marker Sox1 positive cells reach 70% or more, after induction.

Differentiation Potentials of Stem Cells can be Predicted by Analyzing Histone H3K4me3 and H3K27me3 Modification States of Pedigree Differentiation Related Genes To further verify the correlation between histone H3K4me3 and H3K27me3 modification states of differentiation related genes and differentiation potentials of stem cells, the inventor further analyzes the histone modifications of adipogenic and osteogenic pedigree differentiation related genes in adipose derived MSCs (aMSCs) and bone marrow derived MSCs (bMSCs) with ChIP-PCR, and compares their differentiation potentials towards these two pedigrees above. The results of histone methylation analysis show that osteogenic genes RUNX2, BMP2, Smad5, TAZ, Wnt5a and BMPR2 in aMSCs exhibit activating modification, MSX2 and BMP4 exhibit bivalent modification; all genes in bMSCs exhibit activating modification, except that MSX2 exhibits bivalent modification in which H3K4me3 is dominant (FIG. 5A). Adipogenic genes ERK5, GSK3α, GSK3β, C/EBPδ, PPARγ and C/EBPβ in aMSCs exhibit activating modification, except that C/EBPα exhibits bivalent modification; whereas in bMSCs mainly exhibit bivalent modification (FIG. 5B). Under the same induction conditions, the comparison of osteogenic and adipogenic differentiation in aMSCs and bMSCs shows that, on the 8th day of osteogenic induction, differentiation ratios of aMSCs and bMSCs are 50% and 65% respectively, expressions of marker genes ALP and OPN show statistically differences; on the 8th day of adipogenic induction, differentiation ratios of aMSCs and bMSCs are 80% and 27% respectively, expressions of marker genes LPL and AP2 show statistically differences (FIG. 5C).

As seen, although adipogenesis and osteogenesis related genes in MSCs derived from two different origins exhibit H3K4me3 or bivalent modification, the ratio of H3K4me3 modification of adipogenesis related genes in aMSCs is significantly higher than that in bMSCs. This is consistent with the result that, when compared with aMSCs, bMSCs shows more difficulty in differentiating towards adipogenic pedigree; histone methylation activating modification of osteogenesis related genes in bMSC are similar to those in aMSCs. This is consistent with the result observed that both bMSCs and aMSCs have similar differentiation potential towards osteogenic pedigree. The analysis of histone modification of differentiation related genes in MSCs derived from different origins and the comparison results of differentiation potentials further demonstrate that the prediction of differentiation potential of stem cells, by using histone H3K4me3 and H3K27me3 modification states of pedigree differentiation related genes as epigenetic modification markers, is feasible.

Example 4

Differentiation Degree of Cells can be Predicted by Dynamic Analysis of Histone H3K4me3 and H3K27me3 Modification States of Differentiation Stage Related Genes It is proved that differentiation potential of stem cells can be predicted by using histone methylation analysis as epigenetic modification label. The inventor then analyzes the dynamic changes of histone methylation modification of related transcription factors before and after the differentiation of Flk1+ MSCs by using ChIP-PCR. The results show that, during differentiation of Flk1+ MSCs towards neural pedigree, histone modification states of key transcription factors Pax6 and Neurog2 change from H3K27me3 inhibiting state into bivalent modification; as for Neurod2, change from H3K27me3 inhibiting state into activating state; as for Gfra2, change from bivalent state into activating state; as for Tlx2 and Msi1, change from K27 modification-dominant bivalent modification state into K4-dominant state; as for Gfra1, change from absence of modification into bivalent state; the expressions of Neurog2, Pax6, Tlx2, Neurod2 and Msi1 are significantly up-regulated. During differentiation of Flk1+ MSCs towards adipogenic pedigree, along with the transient up-regulation of expressions of early adipogenic transcription factors C/EBPβ and C/EBPδ, the histone modification states thereof change from H3K4me3 activating state into bivalent state, the expression amount of regulation factor GSK3Δ is increased and then maintained at a relatively high level, and the histone modification is also maintained in constant H3K4me3 activating state; the downstream effector molecule PPARγ of these genes is maintained in constant activating state; whereas, as for C/EBPα, bivalent state is changed into activating state; along with the increasing expression level of PPARγ and C/EBPα, adipogenic differentiation develops smoothly; expressions of marker genes LPL and AP2 are significantly increased. During differentiation of Flk1+ MSCs towards osteogenic pedigree, along with the change of histone modification of early regulation genes from H3K4me3 into bivalent modification, BMP2, TAZ, MSX2, Smad5 and BMPR2 also undergo a dynamic process from expression up-regulation to expression peak occurred at the 4-6$^{th}$ day upon induction, and then from peak to expression down-regulation. Such dynamic expression changes ensure the initiation of osteogenic differentiation, and also contributes to the further mature of osteogenic cell function; osteogenic key gene RUNX2 is maintained in H3K4me3 activating state, and the increasing expression level in turn promotes the expression of downstream target gene OSX and osteogenic marker genes ALP and OPN. Interestingly, the inventor finds that, during the differentiation of Flk1$^+$ MSCs towards adipogenesis, histone modification of osteogenic differentiation related transcription factors RUNX2, TAZ, MSX2, Smad5 and BMPR2 is changed from H3K4me3 activating state into bivalent modification; as for MSX2, histone modification is changed from bivalent modification into inhibiting state; and the expressions of all these genes are down-regulated. While during the differentiation of Flk1$^+$ MSCs towards osteogenesis, histone modification of adipogenic differentiation related transcription factors such as C/EBPβ, C/EBPδ, GSK3δ and PPARγ is changed from H3K4me3 activating state into bivalent modification; as for C/EBPα, histone modification is changed from bivalent modification into H3K27me3 inhibiting state; and the expressions of these genes are also decreased. While during the differentiation of Flk1$^+$ MSCs towards adipogenesis or osteogenesis pedigrees, histone modification of neural differentiation related transcription factors such as MSI1, TLX2 and NES is further inhibited. In terminally differentiated lipoblasts or osteoblasts, the dominant histone modifications of these pedigree differentiation related transcription factors and marker genes are H3K4me3, whereas other pedigrees exhibit H3K27me3. These results suggest that, just before the initiation of differentiation of Flk1$^+$ MSCs towards a specific pedigree, some unknown mechanisms change the histone modification states of related genes so as to activate the expression of genes required by differentiation towards said pedigree and inhibit or block the expression of other pedigrees related factors, thereby allowing the successful differentiation towards a specific pedigree.

According to the dynamic analysis of histone modification above, it can be seen that histone modifications of these pedigree related transcription factors exhibit further activation (i.e. in fashions from inhibition or absence of modification to bivalent modification; from K27-dominant bivalent state to K4-dominant bivalent state; from bivalent state to activating state or maintenance of constant activation etc.) after the differentiation of Flk$^+$ MSCs towards neural, adipogenic and osteogenic pedigrees. The further activated histone modification change mentioned above makes the activation of specific pedigree differentiation related genes or the up-regulation of expressions possible. Not only that, upon the initiation of differentiation of Flk1$^+$ MSCs towards a specific pedigree, histone modification of said pedigree differentiation related genes further become activated, whereas histones of other pedigree differentiation related genes further become a dominant inhibiting modification. This will ensure a satisfying specificity and efficiency of differentiation of stem cells towards specific pedigrees. In summary, during the differentiation of cells towards specific pedigrees, the dynamic changes in histone methylation modifications meet the needs of initiating the activation of related genes at different differentiation stages. The histone methylation modification state of differentiation stage related genes in cells with unknown differentiation degrees can be used to evaluate the differentiation stages of said cells. Therefore, histone methylation modification state analysis can be served as auxiliary indicators for identifying the differentiation stage or maturity of cells.

DISCUSSION

The above research results suggest that different histone methylation modification states of various key pedigree differentiation related genes in different grade of stem/progenitor cells are closely associated with the differentiation potentials of these cells. The analysis of histone methylation of stem/progenitor cells with unknown differentiation potentials can be used to predict the differentiation potentials of these cells. Furthermore, before the initiation of differentiation towards a specific pedigree, under the regulation of some unknown mechanisms, the histone modification states will be rearranged so as to facilitate the activation of differentiation related genes a specific pedigree and maintain differentiation related genes of other pedigrees inactivated, thereby allowing the specificity of directed differentiation. Therefore, the analysis of histone methylation modification of differentiation stage related genes can be used to identify the differentiation stage and maturity of cells. Therefore, the inventor proposes that histone H3K4me3 and H3K27me3 modification states of differentiation related genes are closely associated with the differentiation potentials and differentiation stages of stem cells, and can be used as epigenetic labels for predicting the differentiation potentials, differentiation stages and maturities of stem cells at different grades derived from different origins. The present finding provides a novel standard for better screening and identifying seed cells needed by clinical regeneration and repair treatments of various tissues and organs. Such histone methylation labels are easy to be obtained: at first, genome-wide histone methylation modification profile of stem cells with unknown differentiation potential is obtained by using ChIP-Seq technique, and then the histone H3K4me3 and H3K27me3 modification states of differentiations related genes of one/some pedigrees are specifically analyzed according to the application purpose of said stem cells, and the ChIP-Seq results are further verified by using ChIP-PCR technique, and then the prediction whether or not the stem cells have differentiation potential towards said pedigree can be made. Alternatively, alignment analysis can be done depending on the increasing network database resources obtained from human ESCs, adipose mesenchymal stem cell, hematopoietic stem cell, hematopoietic progenitor cell and mature T cells and the like. According to the difference of the differentiation potentials, stem cells with unknown differentiation potential can be ranked and located along a ranking Pyramid of stem cells, wherein ESCs with differentiation totipotency are located at the top of the Pyramid. Once the genome-wide histone methylation modification profile is obtained with ChIP-Seq technique, a simple and a rapid prediction whether or not these stem cells have differentiation potential towards target pedigree under proper external conditions or micro-environment in vivo can be made. Likewise, based on the analysis of histone methylation modification states of related transcription factors and differentiation stage marker genes during differentiation towards a specific pedigree with ChIP-Seq or ChIP-PCR techniques and by combining the real time and quantified PCR of these transcription factors and marker genes, a good identification of the specific differentiation stage of stem cells can be performed (Note: the more activated (including the change from bivalent modification to H3K4me3 activating modification; or the change from H3K27me3 inhibiting modification to bivalent modification)

the histone methylation state of a certain gene is, the more possibility of being further activated the gene has, since the histone methylation modification changes are ahead of the gene expressions; whereas, the up-regulation or the degree of up-regulation of said genes are controlled under the regulation of its upstream activation factors, cytokines or miRNAs etc.). When stem cells differentiate towards a target pedigree, the analysis of changes of histone modification states of other pedigrees related genes can also be used to identify whether stem cells can specifically differentiate towards target genes.

Therefore, the following procedures are hopeful to become a gold standard for screening seed cells needed by clinical regeneration and repair treatments of various tissues and organs, and for identifying the differentiation stage and differentiation specificity: analyzing histone H3K4me3 and H3K27me3 modification states of related genes with genome-wide ChIP-Seq technique and ChIP-PCR, combining the results obtained from corresponding gene chips, making combinatorial epigenetic detection labels specific for different pedigree key transcription factors, combining the combinatorial application of markers such as genes and non-coding RNA and the like.

REFERENCES

[1] Takahashi K. Yamanaka S. Induction of pluripotent stem cells from mouse embryonic and adult fibroblast cultures by defined factors. Cell, 2006, 126(4): 663-676.
[2] Takahashi K, Tanabe K, Ohnuki M, et al. Induction of pluripotent stem cells from adult human fibroblasts by defined factors. Cell, 2007, 131(5): 861-872.
[3] Brazelton T R, Rossi F M, Keshet G I, Blau H M. From marrow to brain: expression of neuronal phenotypes in adult mice. Science, 2000, 290(5497): 1775-1779
[4] Jiang Y, jahagirdar B N, Reinardt R L, et al. Pluripotency of mesenchymal stem cells derived from adult marrow. Nature, 200, 418 (6893): 41-49.
[5] Jiang Y. Henderson D. Blackstad M. et al. Neuroectodermal differentiation from mouse multipotent adult progenitor cells. Proc Natl Acad Sci USA, 2003, 100 (supp 1): 11854-11860.
[6] Boggs, B. A., Cheung, P., Heard, E., Spector, D. L., Chinault, A. C., and Allis, C. D. Differentially methylated forms of histone H3 show unique association patterns with inactive human X chromosomes. Nat. Genet. 2002, 30: 73-76.
[7] Peters, A. H., Mermoud, J. E., O'Carroll, D., Pagani, M., Schweizer, D., Brockdorff, N., and Jenuwein, T. Histone H3 lysine 9 methylation is an epigenetic imprint of facultative heterochromatin. Nat. Genet. 2002, 30: 77-80.
[8] Plath, K., Fang, J., Mlynarczyk-Evans, S. K., Cao, R., Worringer, K. A., Wang, H., de la Cruz, C. C., Otte, A. P., Panning, B., and Zhang, Y. Role of histone H3 lysine 27 methylation in X inactivation. Science. 2003, 300: 131-135.
[9] Silva, J., Mak, W., Zvetkova, I., Appanah, R., Nesterova, T. B., Webster, Z., Peters, A. H., Jenuwein, T., Otte, A. P., and Brockdorff, N. Establishment of histone h3 methylation on the inactive X chromosome requires transient recruitment of Eed-Enx1 polycomb group complexes. Dev. Cell. 2003, 4:481-495.
[10] Barski, A., et al., High-resolution profiling of histone methylations in the human genome. Cell, 2007. 129(4): 823-37
[11] Martin, C., and Zhang, Y. The diverse functions of histone lysine methylation. Nat. Rev. Mol. Cell Biol. 2005, 6: 838-849.
[12] Schneider, R., Bannister, A. J., Myers, F. A., Thorne, A. W., Crane-Robinson, C., and Kouzarides, T. Histone H3 lysine 4 methylation patterns in higher eukaryotic genes. Nat. Cell Biol. 2003, 6: 73-77.
[13] Schubeler, D., MacAlpine, D. M., Scalzo, D., Wirbelauer, C., Kooperberg, C., van Leeuwen, F., Gottschling, D. E., O'Neill, L. P., Turner, B. M., Delrow, J., et al. (2004). The histone modification pattern of active genes revealed through genome-wide chromatin analysis of a higher eukaryote. 2004, Genes Dev. 18: 1263-1271.
[14] Bernstein, B. E., et al., A bivalent chromatin structure marks key developmental genes in embryonic stem cells. Cell, 2006. 125(2): 315-26.
[15] Xiao Dong Zhao, Xu Han, Joon Lin Chew, Jun Liu, Kuo Ping Chiu, Andre Choo, Yuriy L. Orlov, Wing-Kin Sung, Atif Shahab, Vladimir A. Kuznetsov, Guillaume Bourque, Steve Oh, Yijun Ruan, Huck-Hui Ng, and Chia-Lin Wei. Whole-Genome Mapping of Histone H3Lys4 and 27 Trimethylations Reveals Distinct Genomic Compartments in Human Embryonic Stem Cells. Cell stem cell. 2007, 1: 286-298.
[16] Pan, G., et al., Whole-genome analysis of histone H3 lysine 4 and lysine 27 methylation in human embryonic stem cells. Cell Stem Cell, 2007. 1(3): 299-312.
[17] Mikkelsen, T. S., et al., Genome-wide maps of chromatin state in pluripotent and lineage-committed cells. Nature, 2007. 448(7153): 553-560.
[18] Newport, J. & Kirschner, M. A major developmental transition in early *Xenopus* embryos: II. Control of the onset of transcription. Cell. 1982, 30: 687-696.
[19] Schier, A. F. The maternal-zygotic transition: death and birth of RNAs. Science. 2007, 316: 406-407.
[20] Tadros, W. & Lipshitz, H. D. The maternal-to-zygotic transition: a play in two acts. Development. 2009, 136: 3033-3042.
[21] Nadine L. Vastenhouw, Yong Zhang, Ian G. Woods, Farhad Imam, Aviv Regev, X. Shirley Liu, John Rinn & Alexander F. Schier. Chromatin signature of embryonic pluripotency is established during genome activation. 2010, 464: 922-925.
[22] Roh, T. Y., Cuddapah, S., Cui, K., and Zhao, K. The genomic landscape of histone modifications in human T cells. Proc. Natl. Acad. Sci. USA. 2006, 103, 15782-15787.
[23] Barski, A. and K. Zhao, Genomic location analysis by ChIP-Seq. J Cell Biochem, 2009. 107(1): 11-8.
[24] Park, P. J., ChIP-seq: advantages and challenges of a maturing technology. Nat Rev Genet, 2009. 10(10): 669-680.

What is claimed is:

1. A method for producing a sub-totipotent stem cell product, comprising the following steps:
 A) isolating mesenchymal stem cells from tissue, said tissue is selected from the group consisting of fat, bone marrow, and umbilical cord;
 B) inoculating the isolated mesenchymal stem cells into at least one well of a substrate at a density of 1 cell/well, and cultivating the inoculated mesenchymal stem cells until at least one individual clone is formed;
 C) further cultivating the at least one individual clone for 4-6 hours to produce seed cells with complete adherence to the at least one well;
 D) adding a first inducing medium to the seed cells and culturing the seed cells in the first inducing medium for 1 day, wherein the first inducing medium comprises 5-50 ng/ml activin A, 50-300 ng/ml Wnt3a, 2%-10% FBS and HG-DMEM;

E) replacing the first inducing medium with a second inducing medium and culturing the seed cells in the second inducing medium for 4 days, wherein the second inducing medium comprises 5-50 ng/ml activin A, 20-400 uM RA, 0.1%-50% FBS and HG-DMEM;

F) isolating cells from the second inducing medium wherein the isolated cells which meet the following features are harvested from the isolated cells as the sub-totipotent stem cells product:
  i) Flk1 positive;
  ii) showing epithelioid morphology;
  iii) showing up-regulation of Foxa2, Sox17, Eomes, Gsc, T, Sox1, Pax6, Epcam and Vimentin by a method selected from the group consisting of RT-PCR, immunofluorescence staining detection and Western Blot.

2. The method of claim 1, wherein the first inducing medium comprises 10-30 ng/ml activin A.

3. The method of claim 1, wherein the first inducing medium comprises 100-300 ng/ml Wnt3a.

4. The method of claim 1, wherein the first inducing medium comprises 5-8% FBS.

5. The method of claim 1, wherein the second inducing medium comprises 10-30 ng/ml activin A.

6. The method of claim 1, wherein the second inducing medium comprises 50-200 µM RA.

7. The method of claim 1, further comprising the step:
  G) identifying the methylation modification state of the sub-totipotent stem cell product by detecting either H3K4me3 modification or bivalent modification of both H3K4me3 and H3K27me3 in the following genes: c-Myc, Sall4, Sox2, Klf4, Hoxa1, Gbx2, Six1, Olig3, T, Pgdfrα, Eomes, Tbx6, Mix11, Kdr, Hand1, Gata4, Mesp2, Onecut1, Prox1, Foxa1, Foxa2, Sox7, Sox17, Pdx1, and Gsc.

* * * * *